[12] United States Patent
Welker et al.

US011286231B2

[10] Patent No.: US 11,286,231 B2
[45] Date of Patent: Mar. 29, 2022

[54] HYDROGEN-BONDING COMPOUNDS, COMPOSITIONS COMPRISING THE SAME, AND METHODS OF PREPARING AND USING THE SAME

[71] Applicants: Wake Forest University Health Sciences, Winston-Salem, NC (US); Wake Forest University, Winston-Salem, NC (US)

[72] Inventors: Mark E. Welker, Clemmons, NC (US); Aleksander Skardal, Clemmons, NC (US); Amber N. Weissenfluh, Lemon Grove, CA (US); Surya Banks, Winston-Salem, NC (US)

[73] Assignees: Wake Forest University Health Sciences, Winston-Salem, NC (US); Wake Forest University, Winston-Salem, NC (US)

[ * ] Notice: Subject to any disclaimer, the term of this patent is extended or adjusted under 35 U.S.C. 154(b) by 358 days.

[21] Appl. No.: 16/344,452

[22] PCT Filed: Oct. 26, 2017

[86] PCT No.: PCT/US2017/058531
§ 371 (c)(1),
(2) Date: Apr. 24, 2019

[87] PCT Pub. No.: WO2018/081425
PCT Pub. Date: May 3, 2018

[65] Prior Publication Data
US 2019/0345096 A1 Nov. 14, 2019

Related U.S. Application Data

[60] Provisional application No. 62/413,181, filed on Oct. 26, 2016.

[51] Int. Cl.
| | | |
|---|---|---|
| *C07C 215/50* | (2006.01) |
| *C07C 211/27* | (2006.01) |
| *C07C 235/46* | (2006.01) |
| *C07C 251/24* | (2006.01) |
| *C08B 37/08* | (2006.01) |
| *C08L 89/06* | (2006.01) |
| *A61L 15/28* | (2006.01) |
| *A61L 15/42* | (2006.01) |
| *A61L 27/22* | (2006.01) |
| *A61L 27/24* | (2006.01) |
| *A61L 27/52* | (2006.01) |

[52] U.S. Cl.
CPC .......... *C07C 215/50* (2013.01); *C07C 211/27* (2013.01); *C07C 235/46* (2013.01); *C07C 251/24* (2013.01); *C08B 37/0072* (2013.01); *C08L 89/06* (2013.01); *A61L 15/28* (2013.01); *A61L 15/42* (2013.01); *A61L 27/222* (2013.01); *A61L 27/24* (2013.01); *A61L 27/52* (2013.01)

[58] Field of Classification Search
CPC ... C07C 215/50; C07C 211/27; C07C 235/46; C07C 251/24; C08B 37/0072; C08L 89/06; A61L 15/28; A61L 15/42; A61L 27/222; A61L 27/24; A61L 27/52
See application file for complete search history.

[56] References Cited

U.S. PATENT DOCUMENTS

| | | | | |
|---|---|---|---|---|
| 6,020,422 A | * | 2/2000 | Connors | B41M 7/0009 524/716 |
| 6,479,198 B2 | * | 11/2002 | Makino | G03C 1/42 430/17 |
| 8,414,739 B2 | * | 4/2013 | Kimura | C09C 3/10 162/168.3 |
| 8,575,276 B2 | * | 11/2013 | Lee | C08G 69/40 525/328.2 |
| 8,716,355 B2 | * | 5/2014 | Tsai | A61K 31/06 514/738 |
| 10,052,350 B2 | * | 8/2018 | Niu | A61L 27/26 |
| 10,618,984 B2 | * | 4/2020 | Buffa | C08B 37/00 |
| 2010/0143980 A1 | * | 6/2010 | Balagurunathan | C07H 1/00 435/101 |
| 2010/0330413 A1 | * | 12/2010 | Gong | H01M 50/155 429/163 |
| 2013/0226293 A1 | * | 8/2013 | Venkateswaran | A61F 2/1627 623/6.22 |
| 2014/0342015 A1 | * | 11/2014 | Murphy | A61L 15/40 424/582 |

(Continued)

FOREIGN PATENT DOCUMENTS

| | | | |
|---|---|---|---|
| JP | 61225138 A | * | 10/1986 |
| JP | 02293735 A | * | 12/1990 |
| WO | 2013180458 | | 12/2013 |
| WO | 2016064648 | | 4/2016 |
| WO | 2018071354 A1 | | 4/2018 |
| WO | 2019152767 A1 | | 8/2019 |

OTHER PUBLICATIONS

C. Parris et al., 25 Journal of Organic Chemistry, 331-334 (1960) (Year: 1960).*

(Continued)

*Primary Examiner* — Alexander R Pagano
(74) *Attorney, Agent, or Firm* — Myers Bigel, P.A.

[57] ABSTRACT

Described herein are compounds having a hydrogen-bonding group and optionally a functional group for binding (e.g., covalently binding) the compound to another compound (e.g., hyaluronic acid and/or gelatin). A compound of the present invention may have a structure represented by and/or comprising Formula I, Formula II, Formula III, Formula IV, Formula IV', Formula V, Formula V', Formula VI, Formula VII, and/or Formula VIII as described herein. Compositions including compounds of the present invention along with methods of preparing and using the same are also described herein.

8 Claims, 6 Drawing Sheets

(56) References Cited

U.S. PATENT DOCUMENTS

| | | | |
|---|---|---|---|
| 2016/0082038 A1* | 3/2016 | Gooding | A61K 47/36 |
| | | | 424/130.1 |
| 2016/0296477 A1 | 10/2016 | Tsai et al. | |
| 2017/0107483 A1 | 4/2017 | Pendergraft et al. | |
| 2017/0312306 A1* | 11/2017 | Ranatunga | A61K 9/0024 |
| 2018/0000743 A1 | 1/2018 | Welker et al. | |
| 2018/0273904 A1 | 9/2018 | Skardal | |
| 2018/0291350 A1 | 10/2018 | Murphy et al. | |
| 2018/0320141 A1 | 11/2018 | Atala et al. | |
| 2018/0348203 A1 | 12/2018 | Skardal | |
| 2019/0106673 A1* | 4/2019 | Skardal | A61L 27/50 |
| 2019/0187129 A1 | 6/2019 | Skardal et al. | |
| 2019/0345439 A1 | 11/2019 | Skardal et al. | |
| 2019/0375860 A1 | 12/2019 | Welker et al. | |
| 2020/0048601 A1 | 2/2020 | Skardal et al. | |
| 2020/0108172 A1 | 4/2020 | Skardal et al. | |
| 2020/0376489 A1 | 12/2020 | Porada et al. | |

OTHER PUBLICATIONS

S. Banks et al., Molbank (2021) (Year: 2021).*
T. Heida et al., Polymers (2020) (Year: 2020).*
X. Meng et al., 53 Progress in Polymer Science, 52-85 (2016) (Year: 2016).*
R. Guo et al., 18 Biomarcromolecules, 1356-1354 (2017) (Year: 2017).*
J. Finbloom et al., Journal of the American Chemical Society, 9691-9697 (2017) (Year: 2017).*
Z. Xu et al., ACS Biomaterials Science and Engineering, 2276-2291 (2018) (Year: 2018).*
Abdel-Aziz et al. "Inhibitory activities against topoisomerase I & II by polyhydroxybenzoyl amide derivatives and their structure-activity relationship" Bioorganic & Medicinal Chemistry Letters, 14:1669-1672 (2004).
Brevitt et al. "Synthesis and in Vitro Evaluation of Two Progressive Series of Bifunctional Polyhydroxybenzamide Catechol-O-methyltransferase Inhibitors" Journal of Medicinal Chemistry, 40(13):2035-2039 (1997).
Galliani et al. "Aromatic Hydroxylation of Benzylamides by Potassium Superoxide" Tetrahedron, 37:2313-2317 (1981).
International Search Report and the Written Opinion of the International Searching Authority corresponding to International Patent Application No. PCT/US2017/058531 (13 pages) (dated Feb. 22, 2018).
Kiviranta et al. "N,N'-Bisbenzylidenebenzene-1,4-diamines and N,N'-Bisbenzylidenenaphthalene-1,4-diamines as Sirtuin Type 2 (SIRT2) Inhibitors" Journal of Medicinal Chemistry, 49:7907-7911 (2006).
Li et al. "Synthesis of [2]Catenanes by Template-Directed Clipping Approach" The Journal of Organic Chemistry, 77:7129-7135 (2012).
Stodola, Frank H. "A New Type of Basic Amide Hydrolysis, Characterized by Alkyl-Nitrogen Fission" The Journal of Organic Chemistry, 37(2):178-186 (1972).
Amsden, Brian "Solute Diffusion within Hydrogels. Mechanisms and Models" Macromolecules, 31:8382-8395 (1998).
Amsden et al. "Diffusion characteristics of calcium alginate gels" Biotechnology and Bioengineering, 65(5):605-610 (1999).
Annabi et al. "Surgical Materials: Current Challenges and Nano-enabled Solutions" Nano Today, 9(5):574-589 (2014).
Annabi et al. "Elastic sealants for surgical applications" European Journal of Pharmaceutics and Biopharmaceutics, 95(Pt. A):27-39 (2015).
Augst et al. "Alginate hydrogels as biomaterials" Macromolecular Bioscience, 6(8):623-633 (2006).
Augustin et al. "Effects of microencapsulation on the gastrointestinal transit and tissue distribution of a bioactive mixture of fish oil, tributyrin and resveratrol" Journal of Functional Foods, 3(1):25-37 (2011).
Barrett et al. "Mechanically Robust, Negative-Swelling, Mussel-Inspired Tissue Adhesives" Advanced Healthcare Materials, 2(5):745-755 (2013).

Batchelor et al. "Reduced plasma half-life of radio-labelled 25-hydroxyvitamin D3 in subjects receiving a high-fibre diet" British Journal of Nutrition, 49:213-216 (1983).
Borke et al. "Optimized triazine-mediated amidation for efficient and controlled functionalization of hyaluronic acid" Carbohydrate Polymers, 116:42-50 (2015).
Bowersock et al. "Oral vaccination of animals with antigens encapsulated in alginate microspheres" Vaccine, 17:1804-1811 (1999).
Brubaker et al. "Enzymatically Degradable Mussel-Inspired Adhesive Hydrogel" Biomacromolecules, 12:4326-4334 (2011).
Burdick et al. "Hyaluronic Acid Hydrogels for Biomedical Applications" Advanced Materials, 23(12):H41-H56 (2011).
Chen et al. "Synthesis and biological evaluation of hydroxyl-substituted Schiff-bases containing ferrocenyl moieties" Dalton Transactions, 42:15678-15686 (2013).
Cheng et al. "Antioxidant and antiproliferative activities of hydroxyl-substituted Schiff bases" Bioorganic & Medicinal Chemistry Letters, 20(8):2417-2420 (2010).
Darrabie et al. "Characteristics of Poly-L-Ornithine-coated alginate microcapsules" Biomaterials, 26(34):6846-6852 (2005).
Deidda et al. "Self-Assembled Amyloid Peptides with Arg-Gly-Asp (RGD) Motifs As Scaffolds for Tissue Engineering" ACS Biomaterials Science & Engineering, 3(7):1404-1416 (2017).
Doraiswamy et al. "Inkjet Printing of Bioadhesives" Journal of Biomedical Materials Research Part B, 89B:28-35 (2009).
Duraine et al. "Biomechanical evaluation of suture holding properties of native and tissue engineered articular cartilage" Biomechanics and Modeling in Mechanobiology, 14(1):73-81 (2015).
Elia et al. "Stimulation of In Vivo Angiogenesis by In Situ Cross-linked, Dual Growth Factor-loaded, Glycosaminoglycan Hydrogels" Biomaterials, 31(17):4630-4638 (2010).
Faion et al. "Ethyl-2-cyanoacrylate as a sealant after partial cecum resection in rattus norvegicus albinus" Journal of Brazilian College of Surgeons, 38(1):045-053 (2011).
Fairbanks et al. "Thiol-Yne Photopolymerizations: Novel Mechanism, Kinetics, and Step-Growth Formation of Highly Cross-Linked Networks" Macromolecules, 42(1):211-217 (2009).
Ferreira et al. "Development of a new photocrosslinkable biodegradable bioadhesive" International Journal of Pharmaceutics, 352(1-2):172-181 (2008).
Follain et al. "Coupling of amines with polyglucuronic acid: Evidence for amide bond formation" Carbohydrate Polymers, 74:333-343 (2008).
Fu et al. "Improvement of endothelial progenitor outgrowth cell (EPOC)-mediated vascularization in gelatin-based hydrogels through pore size manipulation" Acta Biomaterialia, 58:225-237 (2017).
Gandhi et al. "Alginate-based strategies for therapeutic vascularization" Therapeutic Delivery, 4(3):327-341 (2013).
Gao et al. "FeBr3-Catalyzed Tandem Reaction of N-Propargylamides with Disulfides or Diselenides for the Synthesis of Oxazole Derivatives" Synlett, 27(7):1110-1115 (2016).
Glickman et al. "A polymeric sealant inhibits anastomotic suture hole bleeding more rapidly than gelfoam/thrombin: results of a randomized controlled trial" Archives of Surgery, 137(3):326-331 (2002).
Grinstaff, Mark W. "Designing Hydrogel Adhesives for Corneal Wound Repair" Biomaterials, 28(35):1-18 (2007).
Hino et al. "Transmission of symptomatic parvovirus B19 infection by fibrin sealant used during surgery" British Journal of Haematology, 108:194-195 (2000).
Hospodiuk et al. "The bioink: A comprehensive review on bioprintable materials" Biotechnology Advances, 3(2):217-239 (2017).
International Preliminary Report on Patentability corresponding to International Patent Application No. PCT/US2017/058531 (10 pages) (dated May 9, 2019).
Jackson et al. "Fibrin sealants in surgical practice: An overview" The American Journal of Surgery, 182(2):S1-S7 (2001).
Jenkins et al. "Molecular Weight Effects upon the Adhesive Bonding of a Mussel Mimetic Polymer" ACS Applied Materials & Interfaces, 5(11):5091-5096 (2013).
Kanellos et al. "Sutureless colonic anastomosis in the rat: a randomized controlled study" Techniques in Coloproctology, 6(3):143-146 (2002).

(56) References Cited

OTHER PUBLICATIONS

Kawamura et al. "Frequency of Transmission of Human Parvovirus B19 Infection by Fibrin Sealant Used During Thoracic Surgery" The Annals of Thoracic Surgery, 73:1098-1100 (2002).
Kendall et al. "Immunoisolation techniques for islet cell transplantation" Expert Opinion In Biological Therapy, 2(5):503-511 (2002).
Lau, Hung "Fibrin Sealant Versus Mechanical Stapling for Mesh Fixation During Endoscopic Extraperitoneal Inguinal Hernioplasty: A Randomized Prospective Trial" Annals of Surgery, 242(5):670-675 (2005).
Lee et al. "Bioinspired, Calcium-Free Alginate Hydrogels with Tunable Physical and Mechanical Properties and Improved Biocompatibility" Biomacromolecules, 14(6):2004-2013 (2013).
Lee et al. "Bio-inspired Nanoparticulate Medical Glues for Minimally Invasive Tissue Repair" Advanced Healthcare Materials, 4(16):2587-2596 (2015).
Leggat et al. "Surgical Applications of Cyanoacrylate Adhesives: A Review of Toxicity" ANZ Journal of Surgery, 77(4):209-213 (2007).
Lin et al. "Adhesion mechanisms of the mussel foot proteins mfp-1 and mfp-3" Proceedings of the National Academy of Sciences, 104(10):3782-3786 (2007).
Lin et al. "Monitoring the Long-Term Degradation Behavior of Biomimetic Bioadhesive using Wireless Magnetoelastic Sensor" IEEE Transactions on Biomedical Engineering, 62(7):1838-1842 (2015).
Mandal et al. "Microencapsulation of Bacterial Cells by Emulsion Technique for Probiotic Application" Cell Microencapsulation, Chapter 22, pp. 273-279 (2016).
Mehdizadeh et al. "Injectable Citrate-Based Mussel-Inspired Tissue Bioadhesives With High Wet Strength for Sutureless Wound Closure" Biomaterials, 33(32)7972-7983 (2012).
Mizrahi et al. "Elasticity and safety of alkoxyethyl cyanoacrylate tissue adhesives" Acta Biomaterialia, 7(8):3150-3157 (2011).
Montanaro et al. "Cytotoxicity, blood compatibility and antimicrobial activity of two cyanoacrylate glues for surgical use" Biomaterials, 22:59-66 (2001).
Nador et al. "Coordination polymer particles with ligand-centred pH-responses and spin transition" Chemical Communications, 50:14570-14572 (2014).
Nose et al. "A sutureless technique using cyanoacrylate adhesives when creating a stoma for extremely low birth weight infants" SpringerPlus, 5(198):1-5 (2016).
Oliva et al. "Natural Tissue Microenvironmental Conditions Modulate Adhesive Material Performance" Langmuir, 28(43):15402-15409 (2012).
Olivi et al. "Tandem amine propargylation-Sonogashira reactions: new three-component coupling leading to functionalized substituted propargylic amines" Tetrahedron Letters, 45(12):2607-2610 (2004).
Opara, Emmanuel C. "Applications of Cell Microencapsulation" Methods in Molecular Biology, 1479:23-39 (2017).
Oudshoorn et al. "Synthesis and characterization of hyperbranched polyglycerol hydrogels" Biomaterials, 27(32):5471-5479 (2006).
Pascual et al. "Cytotoxicity of Cyanoacrylate-Based Tissue Adhesives and Short-Term Preclinical In Vivo Biocompatibility in Abdominal Hernia Repair" PLoS One, 11(6):e0157920 (2016).
Peattie et al. "Effect of Gelatin on Heparin Regulation of Cytokine Release from Hyaluronan-Based Hydrogels" Drug Delivery, 15:389-397 (2008).
Peng et al. "Novel wound sealants: biomaterials and applications" Expert Review of Medical Devices, 7(5):639-659 (2010).
Prestwich et al. "Injectable Synthetic Extracellular Matrices for Tissue Engineering and Repair" Advances in Experimental Medicine and Biology, vol. 585, Chapter 9, pp. 125-133 (2006).
Prestwich et al. "Chemically-Modified HA for Therapy and Regenerative Medicine" Current Pharmaceutical Biotechnology, 9:242-245 (2008).
Ranger et al. "Pneumostasis of experimental air leaks with a new photopolymerized synthetic tissue sealant" The American Surgeon, 63(9):788-795 (1997).
Reis et al. "Alginate Microparticles as Novel Carrier for Oral Insulin Delivery" Biotechnology and Bioengineering, 96(5):977-989 (2007).
Sanders et al. "Mechanical Characterization of a Bi-functional Tetronic Hydrogel Adhesive for Soft Tissues" Journal of Biomedical Materials Research Part A, 103(3):861-868 (2015).
Shin et al. "Tissue Adhesive Catechol-Modified Hyaluronic Acid Hydrogel for Effective, Minimally Invasive Cell Therapy" Advanced Functional Materials, 25(25):3814-3824 (2015).
Skardal et al. "Bioprinting vessel-like constructs using hyaluronan hydrogels crosslinked with tetrahedral polyethylene glycol tetracrylates" Biomaterials, 31:6173-6181 (2010).
Skardal et al. "Dynamically Crosslinked Gold Nanoparticle—Hyaluronan Hydrogels" Advanced Materials, 22:4736-4740 (2010).
Skardal et al. "Photocrosslinkable Hyaluronan-Gelatin Hydrogels for Two-Step Bioprinting" Tissue Engineering: Part A, 16(8):2675-2685 (2010).
Skardal et al. "The generation of 3-D tissue models based on hyaluronan hydrogel-coated microcarriers within a rotating wall vessel bioreactor" Biomaterials, 31:8426-8435 (2010).
Skardal et al. "Bioprinted Amniotic Fluid-Derived Stem Cells Accelerate Healing of Large Skin Wounds" Stem Cells Translational Medicine, 1(11):792-802 (2012).
Skardal et al. "Tissue specific synthetic ECM hydrogels for 3-D in vitro maintenance of hepatocyte function" Biomaterials, 33(18):4565-4575 (2012).
Skardal et al. "Biomaterials for Integration with 3-D Bioprinting" Annals of Biomedical Engineering, 43(3):730-746 (2014).
Skardal et al. "A hydrogel bioink toolkit for mimicking native tissue biochemical and mechanical properties in bioprinted tissue constructs" Acta Biomaterialia, 25:24-34 (2015).
Skardal et al. "Bioprinting Cellularized Constructs Using a Tissue-specific Hydrogel Bioink" Journal of Visualized Experiments, 110(e53606):1-8 (2016).
Skardal et al. "Organoid-on-a-chip and body-on-a-chip systems for drug screening and disease modeling" Drug Discovery Today, 21(9):1399-1411 (2016).
Skardal et al. "A tunable hydrogel system for long-term release of cell-secreted cytokines and bioprinted in situ wound cell delivery" Journal of Biomedical Materials Research Part B, 105B:1986-2000 (2017).
Smejkalova et al. "Structural Characterization of Isomeric Dimers from the Oxidative Oligomerization of Catechol with a Biomimetic Catalyst" Biomacromolecules, 8:737-743 (2007).
Spotnitz, William D. "Fibrin Sealant: The Only Approved Hemostat, Sealant, and Adhesive—a Laboratory and Clinical Perspective" ISRN Surgery, 2014(203943):1-28 (2014).
Vanderhooft et al. "Rheological Properties of Cross-Linked Hyaluronan-Gelatin Hydrogels for Tissue Engineering" Macromolecular Bioscience, 9(1):20-28 (2009).
Vieira et al. "Photocrosslinkable starch-based polymers for ophthalmologic drug delivery" International Journal of Biological Macromolecules, 43:325-332 (2008).
Wagner et al. "The Bioavailability of Vitamin D from Fortified Cheeses and Supplements Is Equivalent in Adults" The Journal of Nutrition, 138:1365-1371 (2008).
Wang et al. "A Temperature-Sensitive, Self-Adhesive Hydrogel to Deliver iPSC-Derived Cardiomyocytes for Heart Repair" International Journal of Cardiology, 190:177-180 (2015).
Weiss et al. "Gastrointestinal Anastomosis With Histoacryl Glue in Rats" Journal of Investigative Surgery, 14:13-19 (2001).
Wirostko et al. "Ophthalmic Uses of a Thiol-Modified Hyaruronan-Based Hydrogel" Advances in Wound Care, 3(11):708-716 (2014).
Yang et al. "A Bio-Inspired Swellable Microneedle Adhesive for Mechanical Interlocking with Tissue" Nature Communications, 4(1702):1-23 (2013).
Zhang et al. "Engineered Extracellular Matrices with Cleavable Crosslinkers for Cell Expansion and Easy Cell Recovery" Biomaterials, 29:4521-4531 (2008).

\* cited by examiner

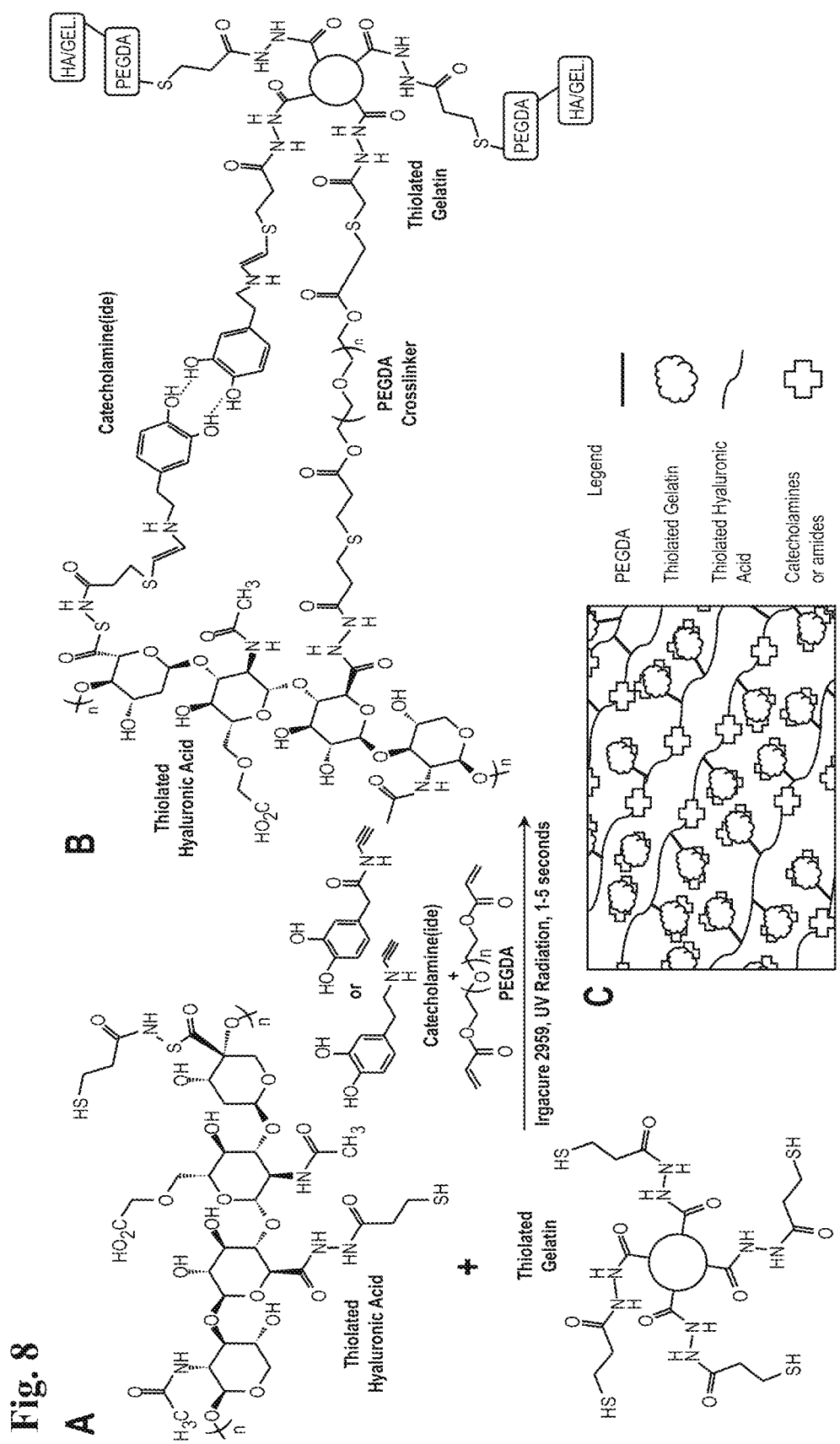

HYDROGEN-BONDING COMPOUNDS, COMPOSITIONS COMPRISING THE SAME, AND METHODS OF PREPARING AND USING THE SAME

RELATED APPLICATION DATA

This application is a 35 U.S.C. § 371 national stage application of International Application No. PCT/US17/58531, filed on Oct. 26, 2017, which claims the benefit of U.S. Provisional Patent Application Ser. No. 62/413,181, filed Oct. 26, 2016, the disclosure of each of which is incorporated by reference herein in their entirety.

FIELD

The present invention generally relates to compounds that include a hydrogen-bonding group along with compositions including such compounds. Also provided are methods of preparing and using the compounds.

BACKGROUND

For the last three decades, biologically-inspired polymers (e.g., biomimetic polymers) and naturally-occurring polymers (e.g., biopolymers) have been researched in the context of developing clinically-relevant hydrogels. During this time the exploration of polymeric hydrogels for use as surgical adhesives has been investigated; however, the translation of these lab bench hydrogel formulations into Food and Drug Administration (FDA) approved products for clinical use has been slow and challenging. As a result, biocompatible hydrogel-based surgical adhesives used to seal wounds after traumatic or surgical injury remain at the cusp of translational medicine research and approved clinical use.

SUMMARY

A first aspect of the present invention is directed to a compound having a structure represented by Formula I:

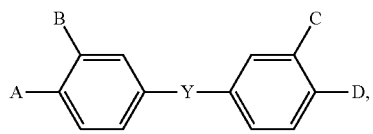

wherein

A, B, C and D are each independently selected from the group consisting of hydrogen, —OH, chlorine, fluorine, —CO$_2$H, —CO$_2$CH$_3$, —NH$_2$, and —NHCOCH$_3$; and Y is a linker having a structure selected from the group consisting of —C≡C(CH$_2$)$_m$—, —C≡C(CH$_2$)$_m$OC(O)—, —C≡C(CH$_2$)$_m$NHC(O)—, —C(O)NH(CH$_2$)$_n$—, —C(O)NH(CH$_2$)$_n$NHC(O)—, —C(O)NH(CH$_2$)$_n$OC(O)—, —CHN(CH$_2$)$_n$—, —CHN(CH$_2$)$_n$NCH—, —C(O)NH(CH$_2$)$_n$R$^1$(CH$_2$)$_n$NCH—, —CHN(CH$_2$)$_n$R$^1$(CH$_2$)$_n$NCH—, and —C(O)NH(CH$_2$)$_n$R$^1$(CH$_2$)$_n$NC(O)—, wherein R$^1$ is selected from a cycloalkyl, cycloalkenyl, and aryl, m is an integer of 0 to 4, and n is each independently an integer of 0 to 11.

Another aspect of the present invention is directed to a compound having a structure represented by Formula II or Formula III:

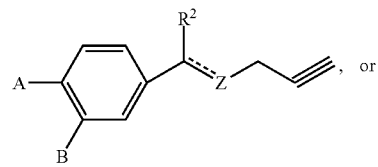

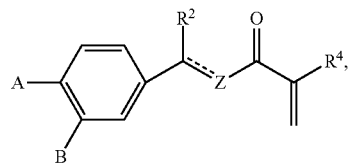

wherein

A and B are each independently selected from the group consisting of hydrogen, —OH, chlorine, fluorine, —CO$_2$H, —CO$_2$CH$_3$, —NH$_2$, and —NHCOCH$_3$;

Z is —NR$_3$(CH$_2$)$_p$—, —O(CH$_2$)$_p$—, —NR$_3$(CH$_2$)$_p$O—, —NR$_3$(CH$_2$)$_p$NR$_3$—;

R$^2$ is hydrogen or =O;

R$^3$ is hydrogen or is absent;

R$^4$ is hydrogen or C$_1$-C$_4$ alkyl; and p is an integer from 0 to 11.

A further aspect of the present invention is directed to a modified polysaccharide comprising at least one polysaccharide unit including a moiety having a structure represented by:

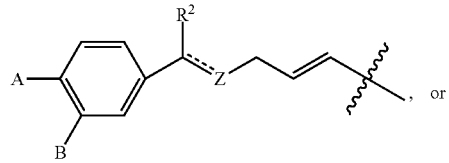

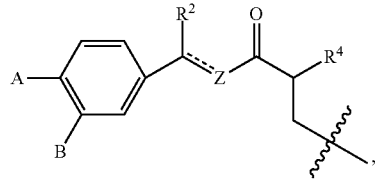

wherein

A and B are each independently selected from the group consisting of hydrogen, —OH, chlorine, fluorine, —CO$_2$H, —CO$_2$CH$_3$, —NH$_2$, and —NHCOCH$_3$;

Z is —NR$_3$(CH$_2$)$_p$—, —O(CH$_2$)$_p$—, —NR$_3$(CH$_2$)$_p$O—, —NR$_3$(CH$_2$)$_p$NR$_3$—;

R$^2$ is hydrogen or =O;

R$^3$ is hydrogen or is absent;

R$^4$ is hydrogen or C$_1$-C$_4$ alkyl; and p is an integer from 0 to 11.

An additional aspect of the present invention is directed to a modified gelatin comprising at least one moiety bound to the gelatin backbone via a thiol linkage to provide a structure represented by:

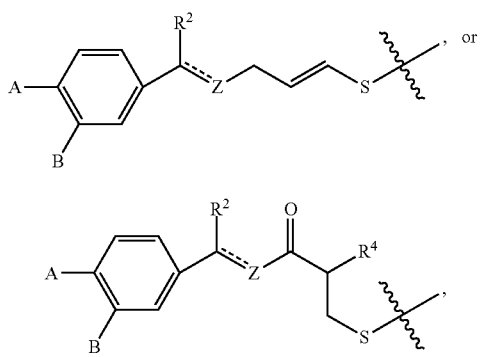

wherein

A and B are each independently selected from the group consisting of hydrogen, —OH, chlorine, fluorine, —CO$_2$H, —CO$_2$CH$_3$, —NH$_2$, and —NHCOCH$_3$;

Z is —NR$_3$(CH$_2$)$_p$—, —O(CH$_2$)$_p$—, —NR$_3$(CH$_2$)$_p$O—, —NR$_3$(CH$_2$)$_p$NR$_3$—;

R$^2$ is hydrogen or =O;

R$^3$ is hydrogen or is absent;

R$^4$ is hydrogen or C$_1$-C$_4$ alkyl; and p is an integer from 0 to 11.

Another aspect of the present invention is directed to a hydrogel comprising a compound of the present invention (e.g., a compound of Formula I, Formula II, Formula III, Formula VI, Formula VII, and/or Formula VIII) and a polysaccharide, collagen, and/or gelatin.

A further aspect of the present invention is directed to a method of increasing the stiffness and/or adhesiveness (e.g., stickiness) of a composition (e.g., a hydrogel), the method comprising combining a compound of the present invention (e.g., a compound of Formula I, Formula II, Formula III, Formula VI, Formula VII, and/or Formula VIII) and a polysaccharide, collagen, and/or gelatin.

Uses of a compound and/or composition (e.g., hydrogel) of the present invention are described herein. In some embodiments, a method of the present invention comprises contacting a compound and/or composition of the present invention to a wound on and/or in a subject and/or the compound and/or composition is suitable for use in wound healing. In some embodiments, a method of the present invention comprises contacting a compound and/or composition of the present invention to opposing surfaces (e.g., of one or more substrates) to bind and/or hold the opposing surfaces together and/or the compound and/or composition is suitable for use as an adhesive.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim and/or file any new claim accordingly, including the right to be able to amend any originally filed claim to depend from and/or incorporate any feature of any other claim or claims although not originally claimed in that manner. These and other objects and/or aspects of the present invention are explained in detail in the specification set forth below. Further features, advantages and details of the present invention will be appreciated by those of ordinary skill in the art from a reading of the figures and the detailed description of the preferred embodiments that follow, such description being merely illustrative of the present invention.

BRIEF DESCRIPTION OF THE DRAWINGS

FIG. 8 shows a (A) schematic for the synthesis of Hystem®+Catecholamine Hydrogel Matrix (1st step) Thiolated HA, thiolated gelatin, PEGDA, and catecholamine are crosslinked via photo-initiated, radical-mediated (catalyzed by Irgacure® 2959) thiol-ene/yne 'click' reaction route; (B) schematic for synthesized hydrogel matrix and intermolecular interactions occurring between catechol amine moieties (2nd Step). The ---- represent hydrogen bond interactions; (C) global schematic of fully-polymerized hydrogel matrix including catecholamine or catecholamides as resting in the PDMS well prior to rheology experimentation (not drawn to scale).

DETAILED DESCRIPTION OF EXAMPLE EMBODIMENTS

Figure 1:
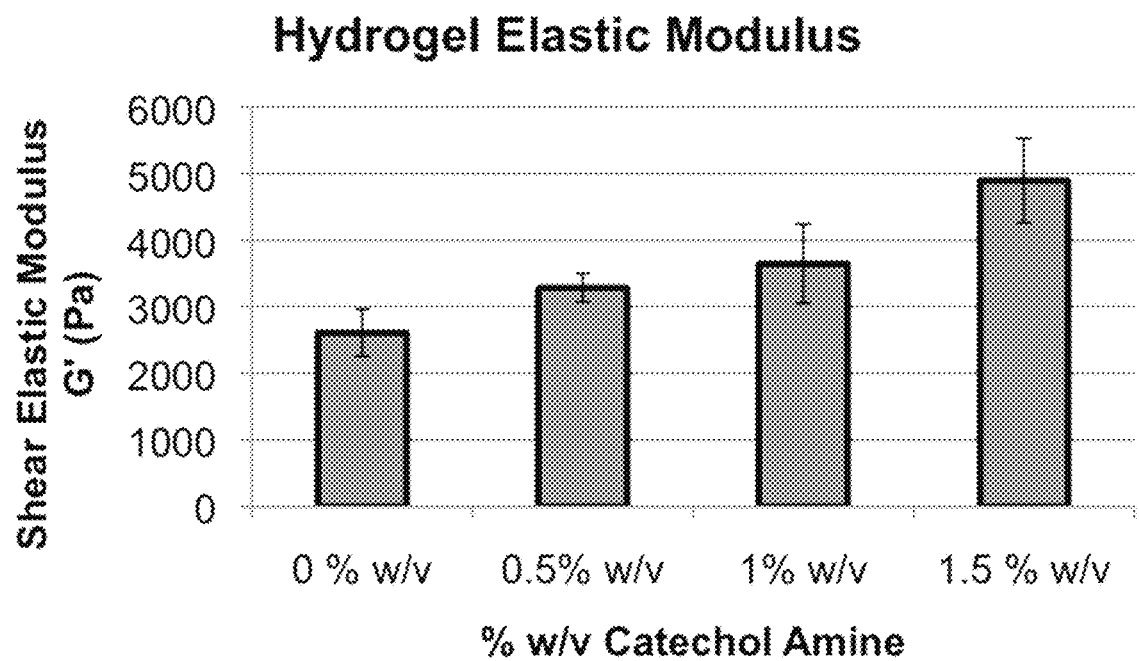
FIG. 1 shows a graph of rheology data showing that shear elastic modulus increases with the amount of catechol amine added to the hydrogel, which may be due to hydrogel bonding.

The present invention is now described more fully hereinafter with reference to the accompanying drawings, in which embodiments of the invention are shown. This invention may, however, be embodied in many different forms and should not be construed as limited to the embodiments set forth herein; rather these embodiments are provided so that this disclosure will be thorough and complete and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a," "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, ±1%, ±0.5%, or even ±0.1% of X. A range provided herein for a measureable value may include any other range and/or individual value therein.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

As used herein, the terms "increase," "increases," "increased," "increasing," and similar terms indicate an elevation in the specified parameter of at least about 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more.

As used herein, the terms "reduce," "reduces," "reduced," "reduction," "inhibit," and similar terms refer to a decrease in the specified parameter of at least about 5%, 10%, 15%, 20%, 25%, 30%, 35%, 40%, 45%, 50%, 55%, 60%, 65%, 70%, 75%, 80%, 85%, 90%, 95%, 97%, or 100%.

Provided herein according to embodiments of the present invention are compounds that may increase the adhesiveness (e.g., stickiness) and/or crosslinking functionality of a composition in which they are present. A compound of the present invention may include a hydrogen-bonding group (e.g., —OH, $CO_2H$, etc.) and optionally a functional group for binding the compound to another compound (e.g., a polysaccharide and/or gelatin). A compound of the present invention may be soluble in water.

In some embodiments, a compound of the present invention has a structure represented by Formula I:

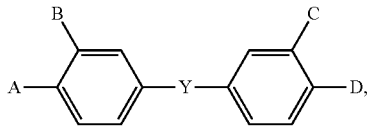

wherein

A, B, C and D are each independently selected from the group consisting of hydrogen, —OH, chlorine, fluorine, —$CO_2H$, —$CO_2CH_3$, —$NH_2$, and —$NHCOCH_3$; and Y is a linker having a structure selected from the group consisting of —C≡C($CH_2$)$_m$—, —C≡C($CH_2$)$_m$OC(O)—, —C≡C($CH_2$)$_m$NHC(O)—, —C(O)NH($CH_2$)$_n$—, —C(O)NH($CH_2$)$_n$NHC(O)—, —C(O)NH($CH_2$)$_n$OC(O)—, —CHN($CH_2$)$_n$—, —CHN($CH_2$)$_n$NCH—, —C(O)NH($CH_2$)$_n$$R^1$($CH_2$)$_n$NCH—, —CHN($CH_2$)$_n$$R^1$($CH_2$)$_n$NCH—, and —C(O)NH($CH_2$)$_n$$R^1$($CH_2$)$_n$NC(O)—, wherein $R^1$ is selected from a cycloalkyl, cycloalkenyl, and aryl, m is an integer of 0 to 4, and n is each independently an integer of 0 to 11.

In some embodiments, at least one, two, three, or four of A, B, C, and D is —OH in the compound of Formula I. In some embodiments, at least one of A and B is —OH and at least one of C and D is —OH in the compound of Formula I. In some embodiments, both A and B are —OH and/or both C and D are —OH in the compound of Formula I.

In some embodiments, at least one, two, three, or four of A, B, C and D is —$NH_2$ or —$NHCOCH_3$ in the compound of Formula I. In some embodiments, at least one, two, three, or four of A, B, C and D is —$CO_2H$ or —$CO_2CH_3$, in the compound of Formula I. In some embodiments, at least one, two, three, or four of A, B, C and D is chlorine or fluorine in the compound of Formula I. In some embodiments, at least one of A and B is —$NH_2$, —$CO_2H$, —$CO_2CH_3$, —$NHCOCH_3$, chlorine, or fluorine and at least one of C and D is —$NH_2$, —$CO_2H$, —$CO_2CH_3$, —$NHCOCH_3$, chlorine, or fluorine in the compound of Formula I. In some embodiments, both A and B are the same and are —$NH_2$, —$CO_2H$, —$CO_2CH_3$, —$NHCOCH_3$, chlorine, or fluorine and/or both C and D are the same and are —$NH_2$, —$CO_2H$, —$CO_2CH_3$, —$NHCOCH_3$, chlorine, or fluorine in the compound of Formula I.

In some embodiments, each n is independently 0, 1, 2, 3, 4, 5, 6, 7, 8, 9, 10, or 11 in the compound of Formula I. In some embodiments, each n is independently 0 to 4 or 8 in the compound of Formula I. In some embodiments, n is 0, 1, 2, or 3 in the compound of Formula I. In some embodiments, m is 0, 1, 2, or 3 in the compound of Formula I.

In some embodiments, Y is —CH($CH_2$)$_n$N$R^1$NCH—, compound of Formula I. In some embodiments, the compound of Formula I has a structure selected from the group consisting of:

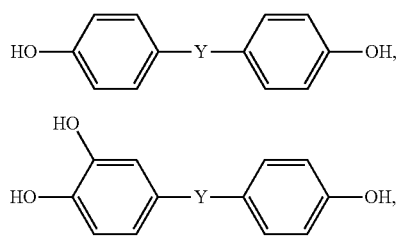

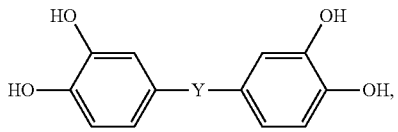

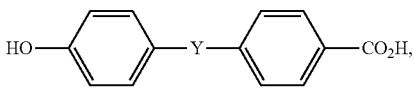

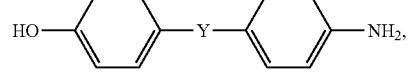

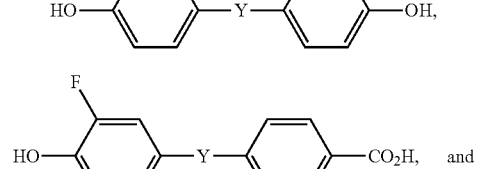

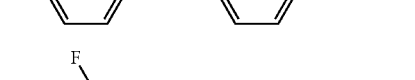

wherein

Y is a linker having a structure selected from the group consisting of —C≡C($CH_2$)$_m$—, —C≡C($CH_2$)$_m$OC(O)—, —C≡C($CH_2$)$_m$NHC(O)—, —C(O)NH($CH_2$)$_n$—, —C(O)NH($CH_2$)$_n$NHC(O)—, —C(O)NH($CH_2$)$_n$OC(O)—, —CHN($CH_2$)$_n$—, —CHN($CH_2$)$_n$NCH—, —C(O)NH($CH_2$)$_n$$R^1$($CH_2$)$_n$NCH—, —CHN($CH_2$)$_n$$R^1$($CH_2$)$_n$NCH—, and —C(O)NH($CH_2$)$_n$$R^1$($CH_2$)$_n$NC(O)—, wherein $R^1$ is selected from a cycloalkyl, cycloalkenyl, and aryl, m is an integer of 0 to 4, and n is each independently an integer of 0 to 11.

In some embodiments, Y is —CHN($CH_2$)$_n$— and n is 0, 1, 2, 3, 4, 5, 6, 7, or 8 in the compound of Formula I. In some embodiments, Y is —C(O)NH($CH_2$)$_n$— and n is 0, 1, 2, 3, 4, 5, 6, 7, or 8 in the compound of Formula I. In some embodiments, Y is —CHN($CH_2$)$_n$$R^1$($CH_2$)$_n$NCH—, $R^1$ is selected from a cycloalkyl, cycloalkenyl, and aryl, and each n is independently 0, 1, 2, 3, 4, 5, 6, 7, or 8 in the compound of Formula I. In some embodiments, $R^1$ is aryl (e.g., phenyl)

and each n is independently 0, 1, 2, or 3 in the compound of Formula I. In some embodiments, each n is the same. In some embodiments, in the compound of Formula I, Y has the following structure:

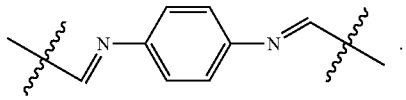 [SMILES: */C=N/c1ccc(/N=C/*)cc1]

In some embodiments, Y is —C(O)NH(CH$_2$)$_n$R$^1$(CH$_2$)$_n$NCH—, R$^1$ is selected from a cycloalkyl, cycloalkenyl, and aryl and each n is independently 0, 1, 2, 3, 4, 5, 6, 7, or 8 in the compound of Formula I. In some embodiments, Y is —C(O)NH(CH$_2$)$_n$R$^1$(CH$_2$)$_n$NC(O)—, R$^1$ is selected from a cycloalkyl, cycloalkenyl, and aryl and each n is independently 0, 1, 2, 3, 4, 5, 6, 7, or 8.

In some embodiments, Y is —C≡C(CH$_2$)$_m$—, —C≡C(CH$_2$)$_m$OC(O)—, or —C≡C(CH$_2$)$_m$NHC(O)—, and m is an integer of 0 to 4 in the compound of Formula I. In some embodiments, Y is —C≡C(CH$_2$)$_m$— and m is 0 in the compound of Formula I. In some embodiments, Y is —C≡C(CH$_2$)$_m$OC(O)— and m is 0, 1, 2, 3, or 4. In some embodiments, Y is —C≡C(CH$_2$)$_m$NHC(O)— and m is 0, 1, 2, 3, or 4 in the compound of Formula I. In some embodiments, Y is —C(O)NH(CH$_2$)$_n$NHC(O)—, —C(O)NH(CH$_2$)$_n$OC(O)—, or —CHN(CH$_2$)$_n$NCH— and n is an integer of 0 to 3, 4, 6, 8, or 11 in the compound of Formula I.

According to some embodiments, a compound of the present invention has a structure represented by Formula II or Formula III:

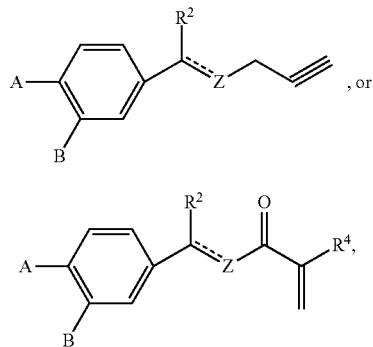

wherein
A and B are each independently selected from the group consisting of hydrogen, —OH, chlorine, fluorine, —CO$_2$H, —CO$_2$CH$_3$, —NH$_2$, and —NHCOCH$_3$;
Z is —NR$_3$(CH$_2$)$_p$—, —O(CH$_2$)$_p$—, —NR$_3$(CH$_2$)$_p$O—, —NR$_3$(CH$_2$)$_p$NR$_3$—;
R$^2$ is hydrogen or =O;
R$^3$ is hydrogen or is absent;
R$^4$ is hydrogen or C$_1$-C$_4$ alkyl; and
p is an integer from 0 to 11.

In some embodiments, the compound of Formula II has a structure selected from the group consisting of:

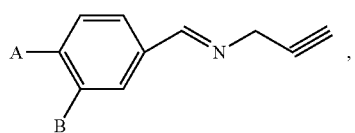

IIa

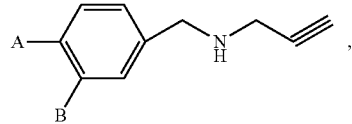

IIb

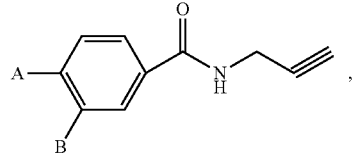

IIc

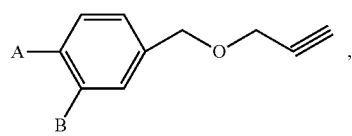

IId

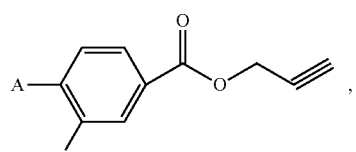

IIe

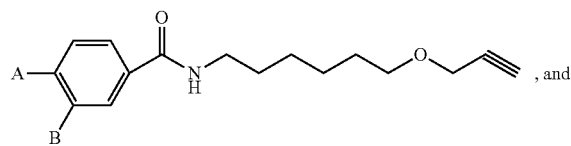

IIf

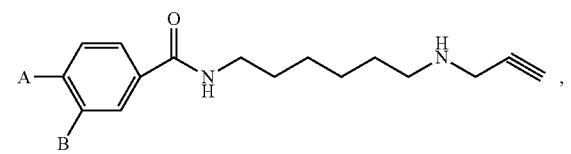

IIg, and wherein A and B are each independently selected from the group consisting of hydrogen,
—OH, chlorine, fluorine, —CO$_2$H, —CO$_2$CH$_3$, —NH$_2$, and —NHCOCH$_3$.

In some embodiments, the compound of Formula III has a structure selected from the group consisting of:

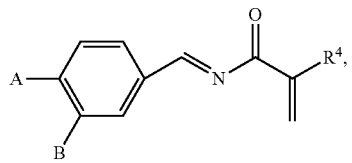

IIIa

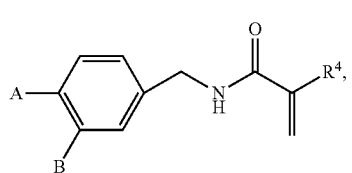

IIIb

-continued

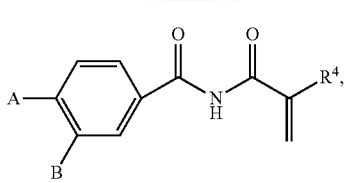
IIIc

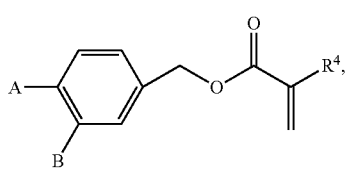
IIId

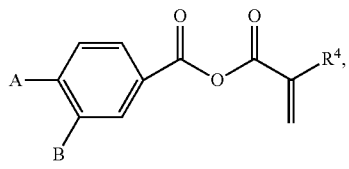
IIIe

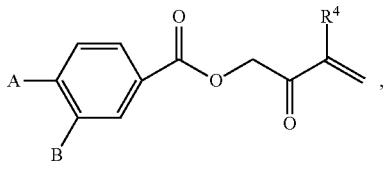
IIIf

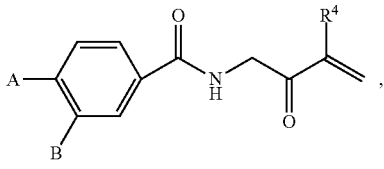
IIIg

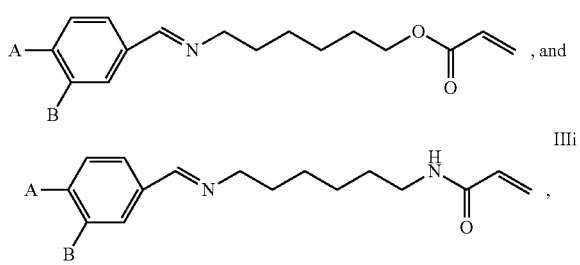
IIIh, and IIIi wherein A and B are each independently selected from the group consisting of hydrogen,
—OH, chlorine, fluorine, —CO$_2$H, —CO$_2$CH$_3$, —NH$_2$, and —NHCOCH$_3$; and
R$^4$ is hydrogen or C$_1$-C$_4$ alkyl.

In some embodiments, R$^4$ is methyl in the compound of Formula III. In some embodiments, R$^4$ is hydrogen in the compound of Formula III. In some embodiments, p is 0, 1, 2, 3, 4, 5, 6, 7, 8, 9, 10, or 11 in the compound of Formula III.

In some embodiments, at least one of A and B is —OH in the compound of Formula II or Formula III. In some embodiments, both A and B are —OH in the compound of Formula II or Formula III. In some embodiments, at least one or both of A and B is —NH$_2$ or —NHCOCH$_3$ in the compound of Formula II or Formula III. In some embodiments, at least one or both of A and B is —CO$_2$H or —CO$_2$CH$_3$ in the compound of Formula II or Formula III. In some embodiments, at least one or both of A and B is chlorine or fluorine in the compound of Formula II or Formula III.

In some embodiments, Z is —NR$_3$— and R$^3$ is hydrogen or is absent in the compound of Formula II or Formula III. In some embodiments, Z is —O— in the compound of Formula II or Formula III. In some embodiments, Z is —NR$_3$CH$_2$— and R$^3$ is hydrogen or is absent in the compound of Formula II or Formula III. In some embodiments, Z is —OCH$_2$— in the compound of Formula II or Formula III. In some embodiments, Z is —NR$_3$CH$_2$— and R$^3$ is hydrogen or is absent in the compound of Formula II or Formula III. In some embodiments, Z is —OCH$_2$— in the compound of Formula II or Formula III.

In some embodiments, the modified polysaccharide may comprise at least one polysaccharide unit including a moiety having a structure represented by Formula IV or Formula V:

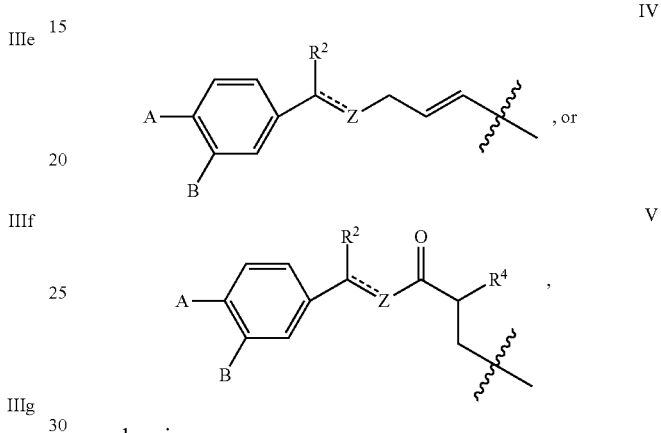
IV, or V wherein
A and B are each independently selected from the group consisting of hydrogen, —OH, chlorine, fluorine, —CO$_2$H, —CO$_2$CH$_3$, —NH$_2$, and —NHCOCH$_3$;
Z is —NR$_3$(CH$_2$)$_p$—, —O(CH$_2$)$_p$—, —NR$_3$(CH$_2$)$_p$O—, —NR$_3$(CH$_2$)$_p$NR$_3$—;
R$^2$ is hydrogen or =O;
R$^3$ is hydrogen or is absent;
R$^4$ is hydrogen or C$_1$-C$_4$ alkyl; and
p is an integer from 0 to 11.

A modified polysaccharide is provided according to some embodiments of the present invention. The modified polysaccharide may comprise a derivative of a compound of the present invention. In some embodiments, the modified polysaccharide may be prepared by combining and/or reacting a polysaccharide and a compound of the present invention.

In some embodiments, the modified polysaccharide may comprise one or more (e.g., 1, 2, 5, 10, 20, 100, or more) polysaccharide unit(s) that include a moiety having a structure represented by Formula IV or Formula V:

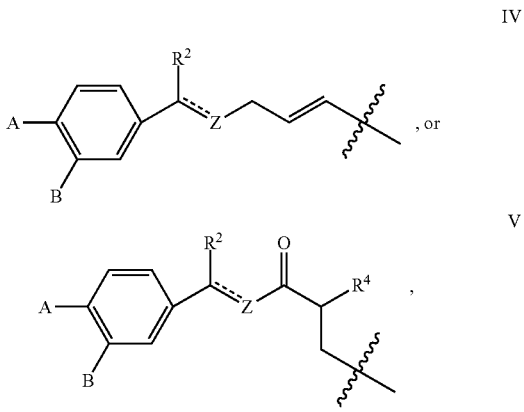
IV, or V wherein

A and B are each independently selected from the group consisting of hydrogen, —OH, chlorine, fluorine, —CO$_2$H, —CO$_2$CH$_3$, —NH$_2$, and —NHCOCH$_3$; Z is —NR$_3$(CH$_2$)$_p$—, —O(CH$_2$)$_p$—, —NR$_3$(CH$_2$)$_p$O—, —NR$_3$(CH$_2$)$_p$NR$_3$—;

R$^2$ is hydrogen or =O;
R$^3$ is hydrogen or is absent;
R$^4$ is hydrogen or C$_1$-C$_4$ alkyl; and
p is an integer from 0 to 11.

In some embodiments, the moiety is bound to the at least one polysaccharide unit via a thiol linkage or via an oxygen linkage. For example, in some embodiments, the moiety is bound to the at least one polysaccharide unit via a thiol linkage to provide a structure represented by Formula IV' or Formula V':

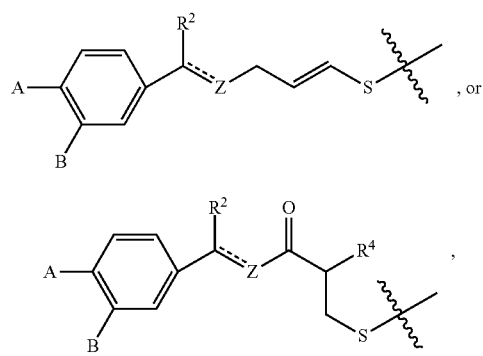

wherein

A and B are each independently selected from the group consisting of hydrogen, —OH, chlorine, fluorine, —CO$_2$H, —CO$_2$CH$_3$, —NH$_2$, and —NHCOCH$_3$; Z is —NR$_3$(CH$_2$)$_p$—, —O(CH$_2$)$_p$—, —NR$_3$(CH$_2$)$_p$O—, —NR$_3$(CH$_2$)$_p$NR$_3$—;

R$^2$ is hydrogen or =O;
R$^3$ is hydrogen or is absent;
R$^4$ is hydrogen or C$_1$-C$_4$ alkyl; and
p is an integer from 0 to 11.

In some embodiments, the moiety bound to the at least one polysaccharide unit has a structure selected from the group consisting of:

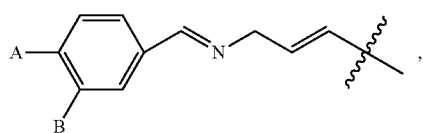

IVa

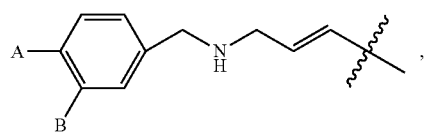

IVb

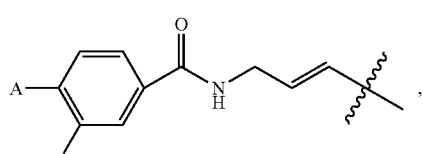

IVc

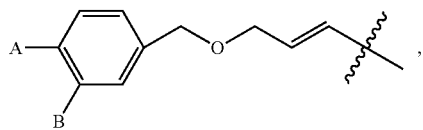

IVd

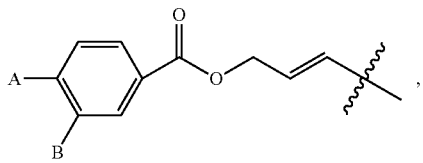

IVe

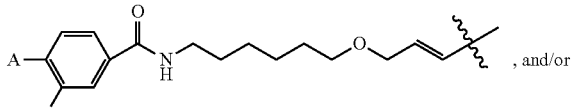

IVf

, and/or

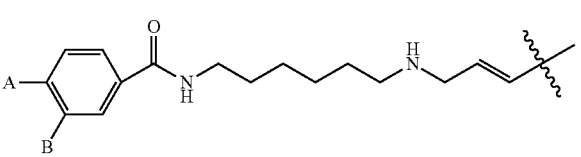

IVg wherein A and B are each independently selected from the group consisting of hydrogen, —OH, chlorine, fluorine, —CO$_2$H, —CO$_2$CH$_3$, —NH$_2$, and —NHCOCH$_3$.

In some embodiments, the moiety bound to the at least one polysaccharide unit has a structure selected from the group consisting of:

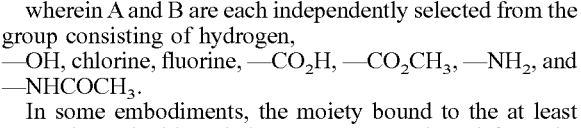

Va

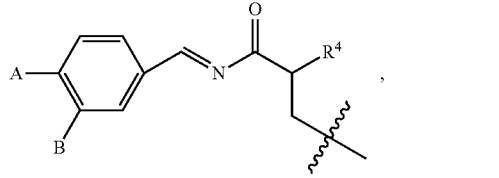

Vb

Vc

Vd

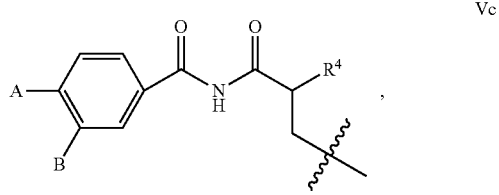

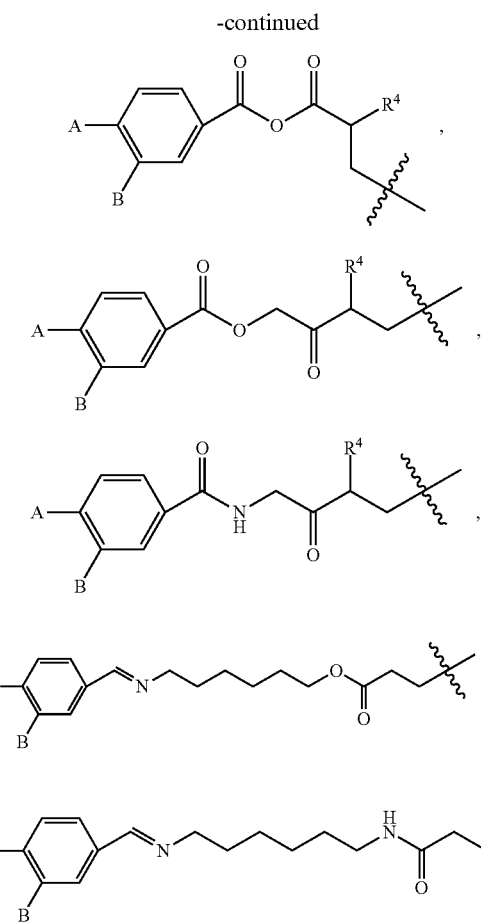

wherein A and B are each independently selected from the group consisting of hydrogen,
—OH, chlorine, fluorine, —CO$_2$H, —CO$_2$CH$_3$, —NH$_2$, and —NHCOCH$_3$; and R$^4$ is hydrogen or C$_1$-C$_4$ alkyl.

In some embodiments, R$^4$ is methyl in the moiety of Formula IV or Formula V. In some embodiments, R$^4$ is hydrogen in the moiety of Formula IV or Formula V.

In some embodiments, at least one or both of A and B is —OH in the moiety of Formula IV or Formula V. In some embodiments, at least one or both of A and B is —NH$_2$ or —NHCOCH$_3$ in the moiety of Formula IV or Formula V. In some embodiments, at least one or both of A and B is —CO$_2$H or —CO$_2$CH$_3$ in the moiety of Formula IV or Formula V. In some embodiments, at least one or both of A and B is chlorine or fluorine in the moiety of Formula IV or Formula V.

In some embodiments, the modified polysaccharide is modified hyaluronic acid, optionally thiolated hyaluronic acid (e.g., hyaluronic acid comprising at least one thiol group bound to one or more hyaluronic acid unit(s)). Thiolated hyaluronic acid has at least one pendant thiol group (i.e., —SH group). In some embodiments, thiolated hyaluronic acid may comprise two or more (e.g., 2, 4, 6, 8, 10, 14, 20, 40, or more) pendant thiol groups. In some embodiments, thiolated hyaluronic acid may be commercially available from ESI BIO (Alameda, Calif.) under the tradename Heprasil® and/or may be obtained from a kit under the tradename HyStem®.

Hyaluronic acid, such as, e.g., the hyaluronic acid used to prepare the thiolated hyaluronic acid, may be produced by bacteria and/or obtained by a fermentation process (e.g., a bacterial fermentation process), such as, e.g., using *Bacillus subtilis* as the host in an ISO 9001:2000 process. In some embodiments, the hyaluronic acid may derived from an animal (e.g., an avian and/or mammal) and/or fermentation source. The hyaluronic acid (e.g., thiolated hyaluronic acid) may have any suitable molecular weight, such as, e.g., a molecular weight from about 80, 100, or 500 kDa to about 1,000, 1,500, or 2,000 kDa. In some embodiments, the hyaluronic acid may have a molecular weight in a range from about 50 kDa to about 200 kDa and/or may have a molecular weight of about 50, 100, 150, or 200 kDa.

According to some embodiments, a modified gelatin and/or collagen of the present invention is provided. The modified gelatin and/or collagen may comprise a derivative of a compound of the present invention. In some embodiments, the modified gelatin and/or collagen may be prepared by combining and/or reacting gelatin and/or collagen and a compound of the present invention.

In some embodiments, modified gelatin and/or collagen may comprise one or more (e.g., 1, 2, 5, 10, 20, 100, or more) moieties having a structure represented by Formula IV or Formula V:

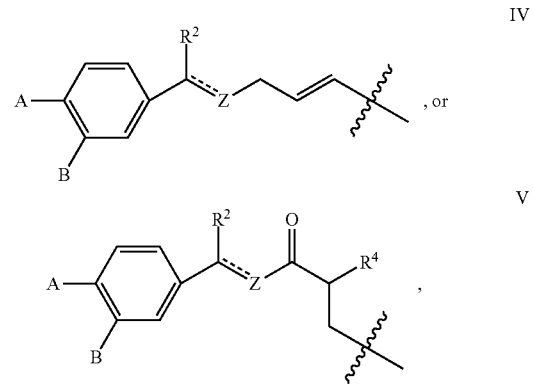

wherein
A and B are each independently selected from the group consisting of hydrogen, —OH, chlorine, fluorine, —CO$_2$H, —CO$_2$CH$_3$, —NH$_2$, and —NHCOCH$_3$;
Z is —NR$_3$(CH$_2$)$_p$—, —O(CH$_2$)$_p$—, —NR$_3$(CH$_2$)$_p$O—, —NR$_3$(CH$_2$)$_p$NR$_3$—;
R$^2$ is hydrogen or =O;
R$^3$ is hydrogen or is absent;
R$^4$ is hydrogen or C$_1$-C$_4$ alkyl; and
p is an integer from 0 to 11.

In some embodiments, the moiety is bound to the gelatin and/or collagen via a thiol linkage or via an oxygen linkage. For example, in some embodiments, the modified gelatin and/or collagen comprises at least one moiety bound to the gelatin backbone and/or collagen backbone via a thiol linkage to provide a structure represented by Formula IV' or Formula V':

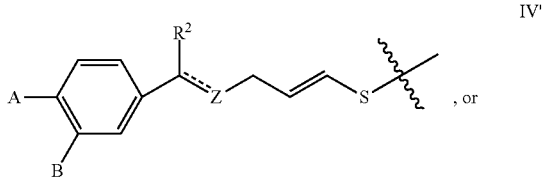

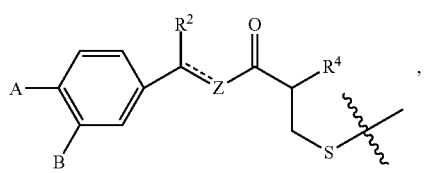

V' wherein

A and B are each independently selected from the group consisting of hydrogen, —OH, chlorine, fluorine, —CO$_2$H, —CO$_2$CH$_3$, —NH$_2$, and —NHCOCH$_3$;

Z is —NR$_3$(CH$_2$)$_p$—, —O(CH$_2$)$_p$—, —NR$_3$(CH$_2$)$_p$O—, —NR$_3$(CH$_2$)$_p$NR$_3$—;

R$^2$ is hydrogen or =O;

R$^3$ is hydrogen or is absent;

R$^4$ is hydrogen or C$_1$-C$_4$ alkyl; and p is an integer from 0 to 11.

The modified gelatin and/or collagen may comprise a moiety having a structure selected from the group consisting of:

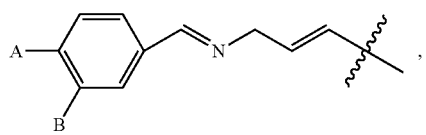

IVa

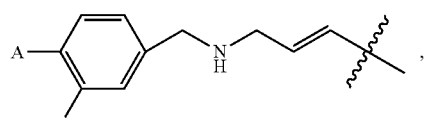

IVb

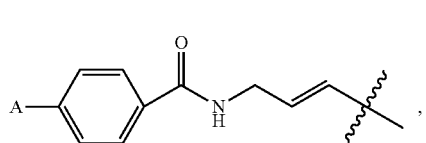

IVc

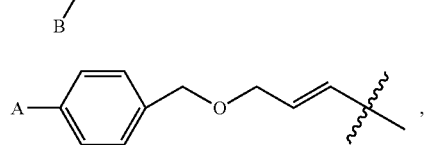

IVd

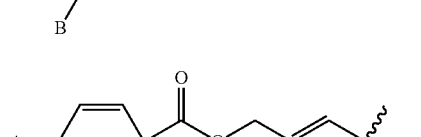

IVe

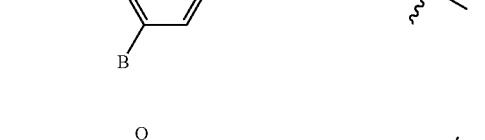

IVf, and/or

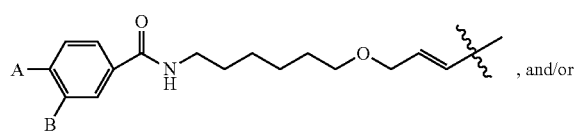

IVg wherein A and B are each independently selected from the group consisting of hydrogen, —OH, chlorine, fluorine, —CO$_2$H, —CO$_2$CH$_3$, —NH$_2$, and —NHCOCH$_3$.

In some embodiments, the modified gelatin and/or collagen may comprise a moiety having a structure selected from the group consisting of:

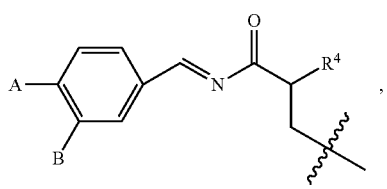

Va

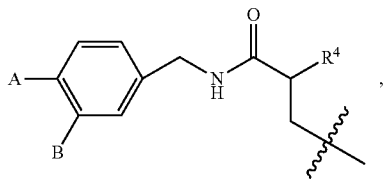

Vb

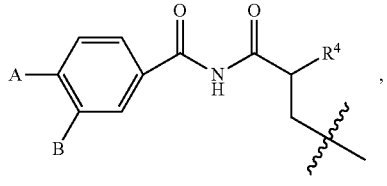

Vc

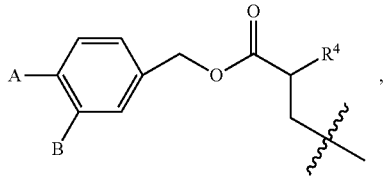

Vd

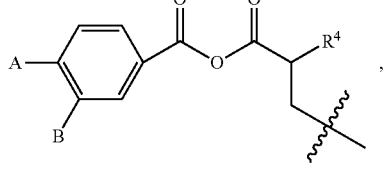

Ve

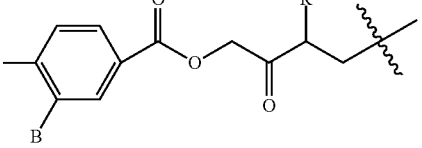

Vf

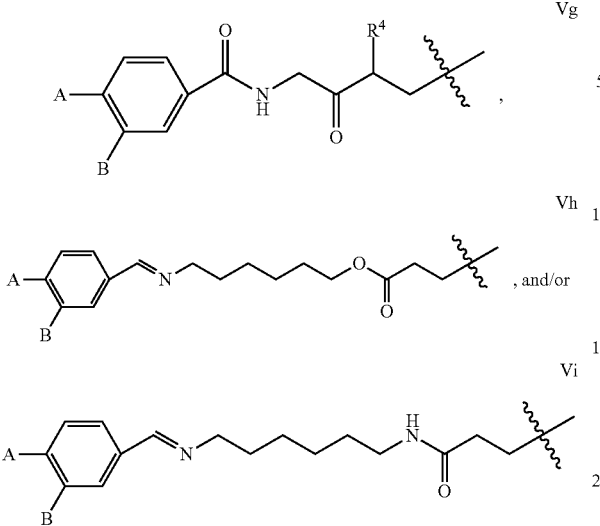

wherein A and B are each independently selected from the group consisting of hydrogen, —OH, chlorine, fluorine, —CO$_2$H, —CO$_2$CH$_3$, —NH$_2$, and —NHCOCH$_3$; and R$^4$ is hydrogen or C$_1$-C$_4$ alkyl.

In some embodiments, the modified gelatin and/or collagen may comprise a moiety of Formula V in which R$^4$ is methyl. In some embodiments, the modified gelatin and/or collagen may comprise a moiety of Formula V in which R$^4$ is hydrogen.

In some embodiments, at least one or both of A and B is —OH in the moiety of Formula IV or Formula V. In some embodiments, at least one or both of A and B is —NH$_2$ or —NHCOCH$_3$ in the moiety of Formula IV or Formula V. In some embodiments, at least one or both of A and B is —CO$_2$H or —CO$_2$CH$_3$ in the moiety of Formula IV or Formula V. In some embodiments, at least one or both of A and B is chlorine or fluorine in the moiety of Formula IV or Formula V.

According to some embodiments, provided is a compound having a structure represented by Formula VI:

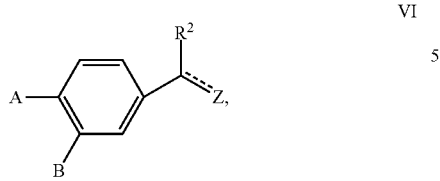

wherein

A and B are each independently selected from the group consisting of hydrogen, —OH, chlorine, fluorine, —CO$_2$H, —CO$_2$CH$_3$, —NH$_2$, and —NHCOCH$_3$; Z is —NR$_3$(CH$_2$)$_p$X, —O(CH$_2$)$_p$X;

R$^2$ is hydrogen or =O;

R$^3$ is hydrogen or is absent;

X is —OH or —NH$_2$; and p is an integer from 0 to 11.

In some embodiments, a compound of Formula VI has a structure selected from the group consisting of:

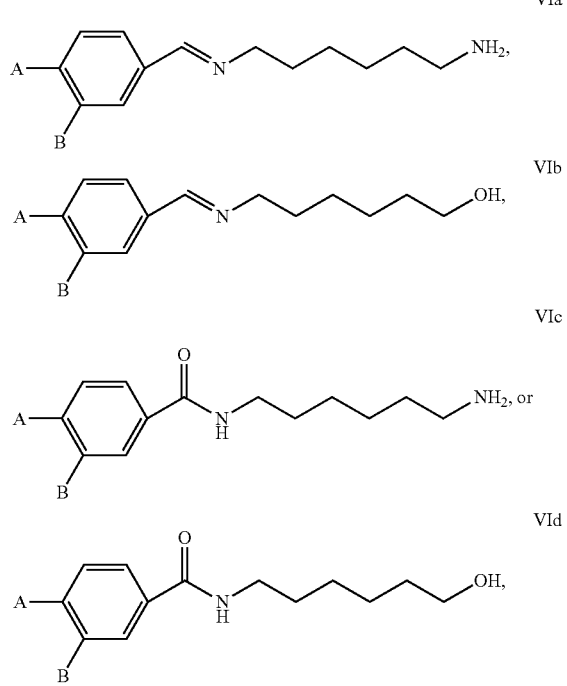

wherein

A and B are each independently selected from the group consisting of hydrogen, —OH, chlorine, fluorine, —CO$_2$H, —CO$_2$CH$_3$, —NH$_2$, and —NHCOCH$_3$.

According to some embodiments, provided is a compound having a structure represented by Formula VII or Formula VIII:

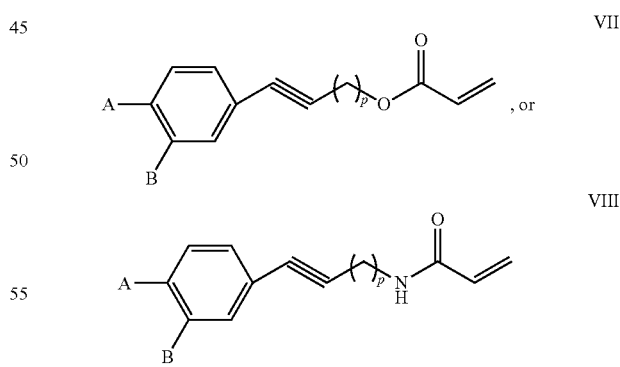

wherein

A and B are each independently selected from the group consisting of hydrogen, —OH, chlorine, fluorine, —CO$_2$H, —CO$_2$CH$_3$, —NH$_2$, and —NHCOCH$_3$; and p is an integer from 0 to 11 (e.g., 0, 1, 2, 3, 4, 5, 6, 7, 8, 9, 10, or 11).

In some embodiments, a modified polysaccharide, gelatin and/or collagen may comprise a moiety having a structure represented by Formula VII' or Formula VIII':

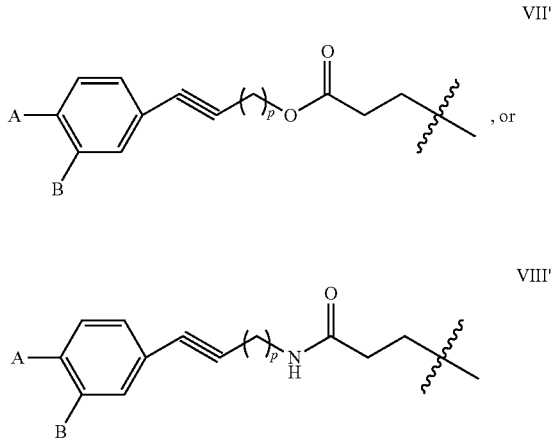

wherein

A and B are each independently selected from the group consisting of hydrogen, —OH, chlorine, fluorine, —CO$_2$H, —CO$_2$CH$_3$, —NH$_2$, and —NHCOCH$_3$; and p is an integer from 0 to 11 (e.g., 0, 1, 2, 3, 4, 5, 6, 7, 8, 9, 10, or 11).

Provided according to some embodiments is a composition of the present invention. A composition of the present invention may comprise a compound of the present invention (e.g., a compound of Formula I, Formula II, Formula III, Formula VI, Formula VII, and/or Formula VIII) and a polysaccharide, gelatin, collagen, and/or a cross-linker. One or more (e.g., 1, 2, 3, 4, 5, 6, 7, or more) different compounds of the present invention may be present in a composition of the present invention. In some embodiments, the composition is a hydrogel.

In some embodiments, a composition of the present invention comprises a modified polysaccharide, gelatin, and/or collagen that comprises a moiety of Formula IV, Formula V, Formula VII' and/or Formula VIII'.

In some embodiments, a composition of the present invention comprises a polysaccharide (e.g., hyaluronic acid) and/or gelatin. In some embodiments, a composition (e.g., a hydrogel) of the present invention is prepared by combining and/or reacting a polysaccharide, collagen, and/or gelatin with a compound of the present invention. In some embodiments, a composition (e.g., a hydrogel) of the present invention is prepared by combining and/or reacting a polysaccharide with a compound of the present invention. The polysaccharide may be hyaluronic acid, optionally thiolated hyaluronic acid. In some embodiments, a composition (e.g., a hydrogel) of the present invention is prepared by combining and/or reacting gelatin and/or collagen with a compound of the present invention.

A compound of the present invention may comprise a hydrogen-bonding group. In some embodiments, a compound of the present invention and/or a moiety thereof binds to a thiol group present in a composition of the present invention (e.g., hydrogel). Within a composition of the present invention, a hydrogen-bonding group (e.g., a catechol group) may form a hydrogen bond such as, e.g., shown in Scheme 1 (arrows), which may increase one or more (e.g., 1, 2, 3, 4, or more) mechanical properties of the composition (e.g., hydrogel).

Scheme 1: Example use and/or reaction of a compound of the present invention and hyaluronic acid (HA) and/or gelatin.

Scheme 1: Example use and/or reaction of a compound of the present invention and hyaluronic acid (HA) and/or gelatin.

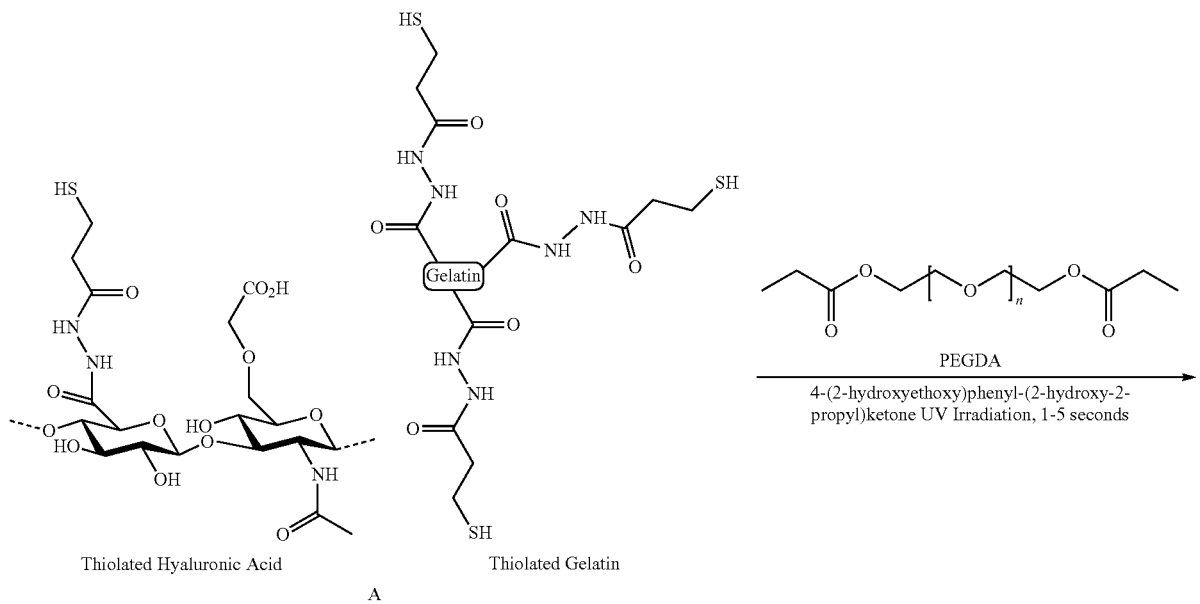

A

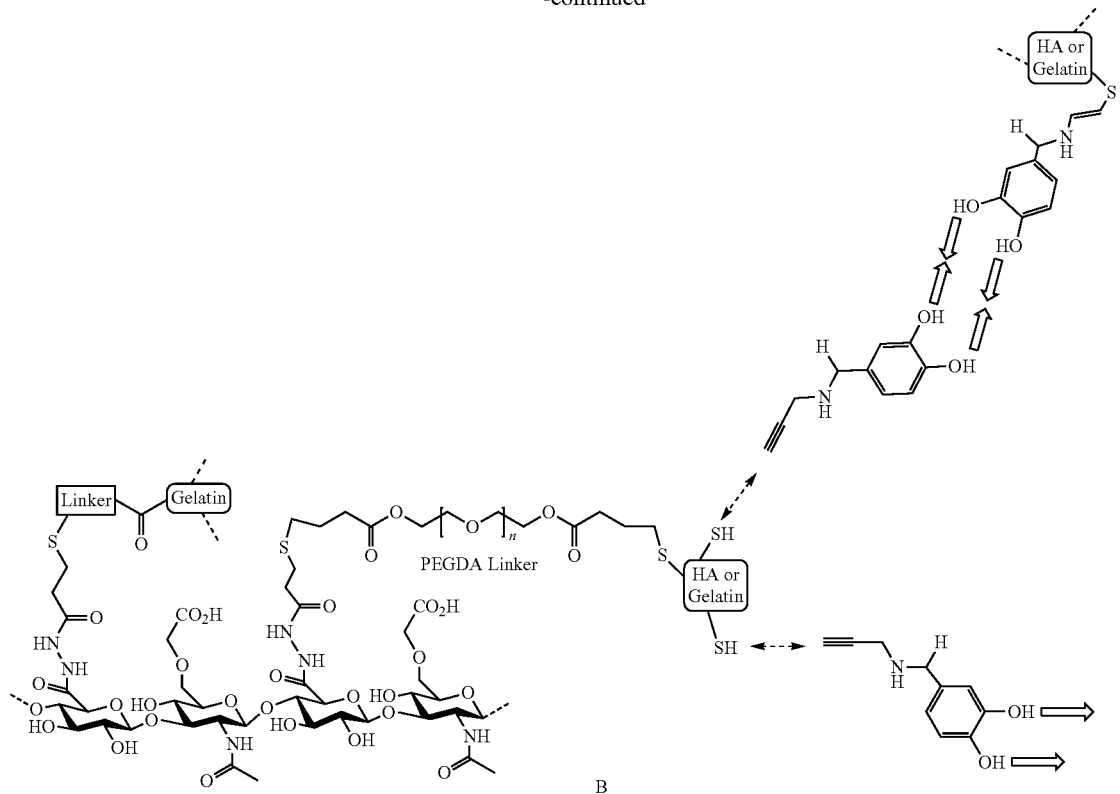

B

One or more (e.g., 1, 2, 3, 4, 5, 6, 7, or more) additional components may be present in a composition of the present invention. For example, in some embodiments, a composition of the present invention may comprise heparin (e.g., heparin sulfate), chondroitin sulfate, alginate sodium salt, and/or elastin. In some embodiments, a composition of the present invention comprises heparin, optionally thiol-modified heparin.

A composition of the present invention may include an initiator (e.g., a thermal or photoinitiator). In some embodiments, the initiator can catalyze a reaction between one or more polysaccharides, collagen, gelatin and/or a compound of the present invention. An example photoinitiator is 4-(2-hydroxyethoxy)phenyl-(2-hydroxy-2-propyl)ketone and/or carboxylated camphorquinone. In some embodiments, the composition may be visible light curable (VLC) and may crosslink and/or cure via blue light (e.g., at about 460 nm). In some embodiments, an initiator (e.g., a photoinitiator) may be present in a composition of the present invention in an amount from about 0.01% to about 0.1% or 1% w/v of the composition. In some embodiments, the initiator is present in the composition in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, or 1% w/v of the composition.

In some embodiments, a composition of the present invention includes a crosslinker. Any suitable crosslinker can be used, including but not limited to a multi-arm thiol-reactive crosslinking agent, such as polyethylene glycol dialkyne, other alkyne-functionalized groups, acrylate or methacrylate groups, and/or other components for elastic modulus modification. Example crosslinkers include, but are not limited to, poly(ethylene glycol) (PEG) diacrylate (DA) (PEGDA) at various molecular weights such as, e.g., from 500 Da to 20 kDa (e.g., 600 Da, 1 kDa, 2 kDA, 3.4 kDa, 5 kDA, and/or 10 kDA), PEG-di-acrylamide (PEGDAA) at various molecular weights such as, e.g., from 500 Da to 20 kDa (e.g., 600 Da, 1 kDa, 2 kDA, 3.4 kDa, 5 kDA, and/or 10 kDA), PEG-di-maleimide (PEGDMal) at various molecular weights such as, e.g., from 500 Da to 20 kDa (e.g., 600 Da, 1 kDa, 2 kDA, 3.4 kDa, 5 kDA, and/or 10 kDA), PEG-di-alkyne at various molecular weights such as, e.g., from 500 Da to 20 kDa (e.g., 600 Da, 1 kDa, 2 kDA, 3.4 kDa, 5 kDA, and/or 10 kDA), 4-Arm PEG acrylate at various molecular weights such as, e.g., from 1 kDa to 30 kDa (e.g., 2 kDA, 5 kDa, 10 kDA, and/or 20 kDA), 4-Arm PEG acrylamide at various molecular weights such as, e.g., from 1 kDa to 30 kDa (e.g., 2 kDA, 5 kDa, 10 kDA, and/or 20 kDA), 4-Arm PEG maleimide at various molecular weights such as, e.g., from 1 kDa to 30 kDa (e.g., 2 kDA, 5 kDa, 10 kDA, and/or 20 kDA), 4-Arm PEG alkyne at various molecular weights such as, e.g., from 1 kDa to 30 kDa (e.g., 2 kDA, 5 kDa, 10 kDA, and/or 20 kDA), 8-Arm PEG acrylate at various molecular weights such as, e.g., from 7 kDa to 50 kDa (e.g., 10 kDA, 20 kDa, and/or 40 kDA), 8-Arm PEG acrylamide at various molecular weights such as, e.g., from 7 kDa to 50 kDa (e.g., 10 kDA, 20 kDa, and/or 40 kDA), 8-Arm PEG maleimide at various molecular weights such as, e.g., from 7 kDa to 50 kDa (e.g., 10 kDA, 20 kDa, and/or 40 kDA), and/or 8-Arm PEG alkyne at various molecular weights such as, e.g., from 7 kDa to 50 kDa (e.g., 10 kDA, 20 kDa, and/or 40 kDA).

A composition of the present invention may have an elastic modulus (i.e., stiffness), at room temperature and atmospheric pressure, that is sufficiently low such that the composition can be manipulated and/or deposited onto a substrate by one or more deposition method(s) (e.g., extrusion deposition, bioprinting, etc.). The elastic modulus, again at room temperature and atmospheric pressure, of the composition may be sufficiently high so that the composition will substantially retain the shape and/or configuration in which it is deposited, optionally until subsequent cross-linking (whether that cross-linking be spontaneous, thermal or photo-initiated, etc.).

In some embodiments, a composition of the present invention may have an elastic modulus (E') from about 0.01, 0.025, 0.05, 0.1, 1, or 5 kiloPascals to about 10, 15, 20, 25, 50, or 100 kiloPascals (kPa). In some embodiments, a composition of the present invention may have an elastic modulus (i.e., stiffness) from about 0.01, 0.025, 0.05, or 0.1 kiloPascals to about 0.5, 1, 5, 10, 15, 20, or 25 kiloPascals, or more, at room temperature and atmospheric pressure. In some embodiments, the composition (e.g., prior to deposition) has a stiffness of from about 10 or 25 Pascals (Pa) to about 500 Pa at room temperature and atmospheric pressure. In some embodiments, the composition (e.g., prior to deposition) has a stiffness of about 10, 25, 50, 75, 100, 150, 200, 250, 300, 350, 400, 450, or 500 Pascals at room temperature and atmospheric pressure. In some embodiments, the composition (e.g., after deposition) has a stiffness from about 0.1 kPa to about 25 kPa at room temperature and atmospheric pressure. In some embodiments, the composition (e.g., after deposition) has a stiffness of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, or 25 kPa at room temperature and atmospheric pressure.

A composition of the present invention may be extrudable. For example, in some embodiments, the composition may be extrudable from a syringe and/or bioprinter. In some embodiments, the composition may be extruded with an applied mechanical stress in a range from about 5 kPa to about 80 kPa. In some embodiments, the composition may be extruded with an applied mechanical stress of about 5, 10, 15, 20, 25, 30, 35, 40, 45, 50, 55, 60, 65, 70, 75, or 80 kPa.

In some embodiments, a composition of the present invention comprises one or more cells. "Cells" and "cell" as used in the present invention are, in general, animal cells, particularly mammalian and primate cells, examples of which include, but are not limited to, human, dog, cat, rabbit, monkey, chimpanzee, cow, pig, goat. The cells may be differentiated at least in part to a particular cell or tissue type, such as liver, intestine, pancreas, lymph node, smooth muscle, skeletal muscle, central nerve, peripheral nerve, skin, immune system, etc. Some cells may be cancer cells. In some embodiments, a cell may express (naturally, or by recombinant techniques) a detectable compound. In some embodiments, cells may be obtained from a subject, such as, for example, a subject or patient undergoing treatment for cancer and/or that has cancer and/or a subject that has a compromised immune system. In some embodiments, a composition of the present invention may comprise a composition and/or hydrogel as described in International Application Publication No. WO 2016/064648, the contents of which are incorporated herein by reference in its entirety.

A composition (e.g., hydrogel) of the present invention may be used to culture one or more cells and/or an organoid and/or a cell and/or tissue construct. In some embodiments, a composition of the present invention may be used to prepare, form, and/or maintain an organoid and/or a cell and/or tissue construct. In some embodiments, a composition of the present invention may be referred to as a "bioink" or a "bioink composition" (both of which are used interchangeably herein), and may comprise one or more live cell(s). However, the compositions of the present invention are not limited to use as a bioink and/or in bioprinting and may be useful in other areas, such as, for example, for an adhesive, wound healing, encapsulation, and/or delivery of an agent. In some embodiments, a composition of the present invention may be used and/or useful in biofabrication applications. In some embodiments, a composition of the present invention is biodegradable. In some embodiments, a composition of the present invention may be bioactive in that it comprises one or more biologically active compounds, such as, e.g., one or more growth factors, cytokines, and/or other naturally-derived bioactive therapeutic agents. In some embodiments, a composition of the present invention is used and/or useful as a cell-delivery vehicle, such as, e.g., in wound healing. In some embodiments, a composition of the present invention may have shear thinning and/or thixatropic properties.

One or more cell(s), tissue(s), and/or organoid(s) may be viable in a composition of the present invention for at least about 1, 2, 3, 4, 6, 7, or more days and/or weeks. In some embodiments, a composition of the present invention may comprise and/or provide one or more cell(s), tissue(s), and/or organoid(s) that are viable and may comprise at least about 75% or more (e.g., about 80%, 85%, 90%, 95% or more) living cells based on the average number of cells present in the composition at about 1, 2, 3, 4, 6, 7, or more days and/or weeks.

A composition of the present invention may comprise collagen (e.g., methacrylated collagen) and/or gelatin in an amount from about 0.5 mg/mL of the composition to about 10 mg/mL of the composition. In some embodiments, collagen and/or gelatin may be present in the composition in an amount of about 0.5, 1, 1.5, 2, 2.5, 3, 3.5, 4, 4.5, 5, 5.5, 6, 6.5, 7, 7.5, 8, 8.5, 9, 9.5, or 10 mg/mL of the composition. In some embodiments, collagen and/or gelatin may be present in the composition in an amount from about 0.1, 0.5, 1, 2, 3, or 4 mg/mL of the composition to about 5, 6, 7, 8, 9, or 10 mg/mL of the composition.

A composition of the present invention may comprise hyaluronic acid (e.g., thiolated hyaluronic acid) in an amount from about 0.1% to about 2% w/v of the composition. In some embodiments, hyaluronic acid may be present in the composition in an amount of about 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, or 2% w/v of the composition.

Water may be present in a composition of the present invention in any suitable amount. In some embodiments, water may be present in an amount of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% by weight of the composition. In some embodiments, the composition is in the form of a hydrogel, optionally an extrudable hydrogel.

In some embodiments, a composition (e.g., hydrogel) of the present invention comprises thiolated HA, thiolated gelatin, and a PEGDA crosslinker. When mixed, the composition may spontaneously gel in about 20-30 minutes at neutral pH and/or nearly instantaneously through photopolymerization. A compound of the present invention (e.g., a catechol amine) may be added to the composition, e.g., in a modular fashion by employing alkyne (as shown in Scheme 1), acrylate, and/or methacrylate functionalization to bind to thiols in the composition (e.g., hydrogel system). Within the composition, the catechol groups may form hydrogen bonds (arrows), which may increase the mechanical properties of the composition (e.g., may increase the elastic modulus of the composition and/or the stickiness of the composition). In some embodiments, a compound of the present invention may interact and/or bond with thiolated HA and/or thiolated gelatin via a thiol alkyne click reaction and/or via Michael addition. In some embodiments, the composition may have excellent and/or improved adhesive properties, tensile strength, provide for control over gelation kinetics, and/or provide for spatial control over location of deposition.

Provided according to some embodiments of the present invention is a method of increasing the stiffness and/or adhesiveness (e.g., stickiness) of a composition (e.g., hydrogel) of the present invention. The stiffness and/or adhesiveness may be increased by a factor of 2, 3, 4, or more compared to the stiffness and/or adhesiveness of the composition without a compound of the present invention. In some embodiments, the method comprises combining a compound of the present invention and a polysaccharide, collagen, and/or gelatin, optionally in water. In some embodiments, the method comprises combining a compound of the present invention and hyaluronic acid, optionally in water. In some embodiments, the compound may be added to a polysaccharide, collagen, and/or gelatin prior to, during, and/or after a crosslinking step and/or reaction. A compound of the present invention may or may not covalently bind to a polysaccharide, collagen, and/or gelatin, and may interact through hydrogen bonding with the polysaccharide, collagen, and/or gelatin. In some embodiments, a compound of the present invention interacts through one or more hydrogen bond(s) with a polysaccharide (e.g., hyaluronic acid), collagen, and/or gelatin and does not covalently bond with the polysaccharide, collagen, and/or gelatin.

A composition of the present invention (e.g., a hydrogel) may be useful in treating and/or healing a wound. In some embodiments, the composition is contacted to a wound on and/or in a subject and/or the composition suitable for use in wound healing.

A composition of the present invention (e.g., a hydrogel) may be useful in an adhesive composition and/or in providing an adhesive composition. The composition may adhere and/or stick to an inert surface, such as, e.g., a polymeric and/or metal surface. In some embodiments, the composition is contacted to opposing surfaces (e.g., opposing surfaces of one or more substrates) to bind and/or hold the opposing surfaces together and/or the composition is suitable for use as an adhesive. In some embodiments, a composition of the present invention achieves and/or meets one or more of the following: 1) maintains adhesive and/or mechanical properties within a physiological environment; 2) polymerizes in situ in aqueous environments; 3) has rheological and/or mechanical properties that match those of a target tissue; 4) is biocompatible; and/or 5) is biodegradable, optionally in a time frame that is suitable and/or compatible with the healing process of a wound.

In some embodiments, a composition of the present invention may be suitable for and/or used in wound closure and/or surgical and/or wound adhesives, and may be an extrudable hydrogel. In some embodiments, a composition of the present invention may be used in place of or with a surgical staple and/or suture in and/or on the skin of a subject. In some embodiments, a composition of the present invention may be pro-regenerative (e.g., may contain one or more bioactive compounds such as, e.g., pro-regenerative cytokines). In some embodiments, a composition of the present invention may be used to treat amniotic sac rupture and/or may be used as a wound healing product and/or wound filler.

A composition of the present invention may have an elastic modulus that is sufficient for an application and/or use as described herein. In some embodiments, the composition has an elastic modulus that is suitable for the composition to stay in place and/or can withstand wear and/or mechanical insults that a wound area may incur during the healing process. In some embodiments, the number of hydrogen-bonding groups (e.g., catechol groups) may be increased in the composition, which may increase the adhesiveness and/or stickiness of the composition. In some embodiments, the total number of hydrogen bonding events within the composition may be tuned and/or modified (e.g., increased or decreased), such as, e.g., by adding a greater amount of a compound of the present invention, and the number of hydrogen bonding events in the composition may provide one or more crosslinks in the composition that are transient, reversible, and/or reformable. In some embodiments, at least a portion or a majority of the crosslinks in the composition may be transient, reversible, and/or reformable, which may allow for applied shear stress during, e.g., extrusion to break these transient bonds, after which the bonds may reform. A composition of the present invention may be biocompatible.

In some embodiments, provided are hyaluronic acid (HA) biomaterial systems. In some embodiments, a compound of the present invention is based on the HA polysaccharide and/or modular small molecule compounds that interface into HA hydrogel systems. This may provide new mechanisms for generating new biomaterial mechanical properties and/or ways to control them. In some embodiments, a compound of the present invention may comprise a catechol functional group, and may provide improved adhesive properties to a HA hydrogel system that is optionally bioactive.

In some embodiments, a compound of the present invention is prepared and/or has a structure as shown in Scheme 2.

Scheme 2: Example preparation and resulting structure of a compound of the present invention.

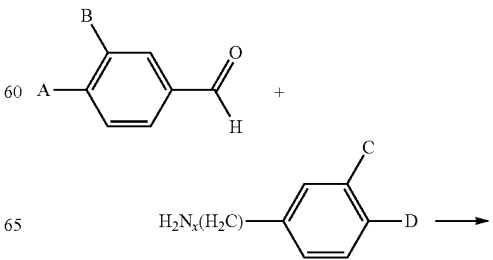

-continued

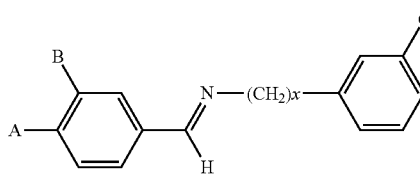

A = D = OH, B = C = H, X = 0, 1, 2
A = B = D = OH, C = H, X = 0, 1, 2
A = B = C = D = OH, X = 0, 1, 2
A = OH, B = C = H, D = CO₂H, X = 0, 1, 2
A = B = OH, C = H, D = CO₂H, X = 0, 1, 2
A = OH, B = C = H, D = NH₂, X = 0, 1, 2
A = B = OH, C = H, D = NH₂, X = 0, 1, 2
A = OH, B = F, C = H, D = OH, X = 0, 1, 2
A = OH, B = F, C = D = OH, X = 0, 1, 2,
A = OH, B = F, C = H, D = CO₂H, X = 0, 1, 2
A = OH, B = F, C = H, D = NH₂, X = 0, 1, 2

In some embodiments, a compound of the present invention is prepared and/or has a structure as shown in Scheme 3.

Scheme 3: Example preparation and resulting structure of a compound of the present invention.

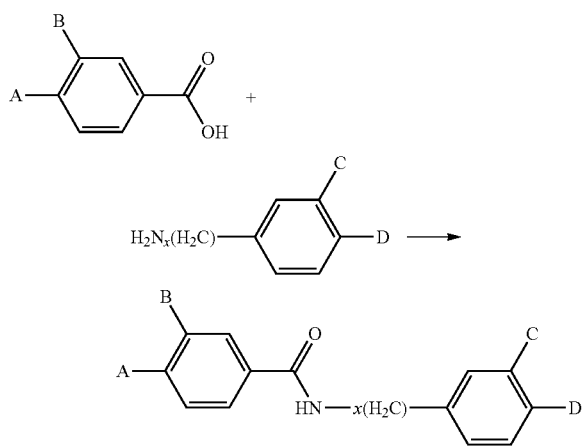

In some embodiments, a compound of the present invention is prepared and/or has a structure as shown in Scheme 4.

Scheme 4: Example preparation and resulting structure of a compound of the present invention.

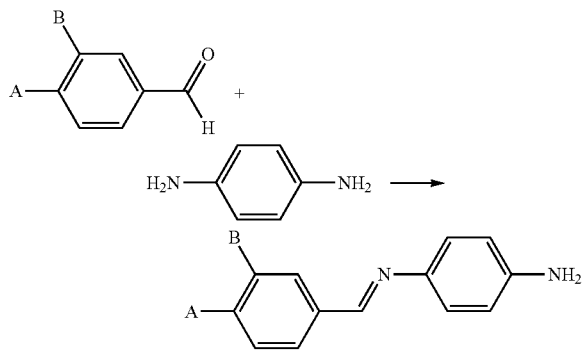

-continued

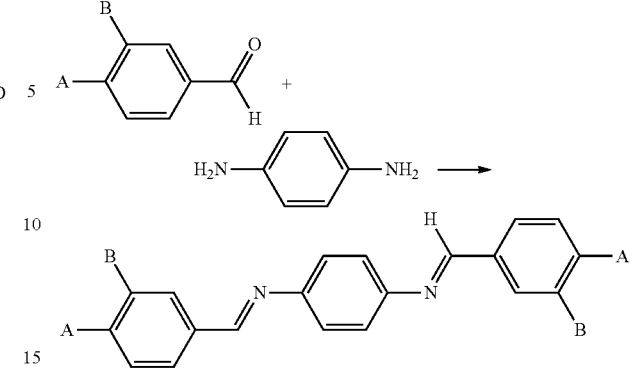

In some embodiments, a compound of the present invention may covalently bond to thiol modified HA, such as, e.g., via a thiol alkyne click reaction. In some embodiments, a compound of the present invention is prepared and/or has a structure as shown in Scheme 5.

Scheme 5: Example preparation and resulting structures of compound of the present invention, with the compound reference numerals referring only to the compounds in this scheme.

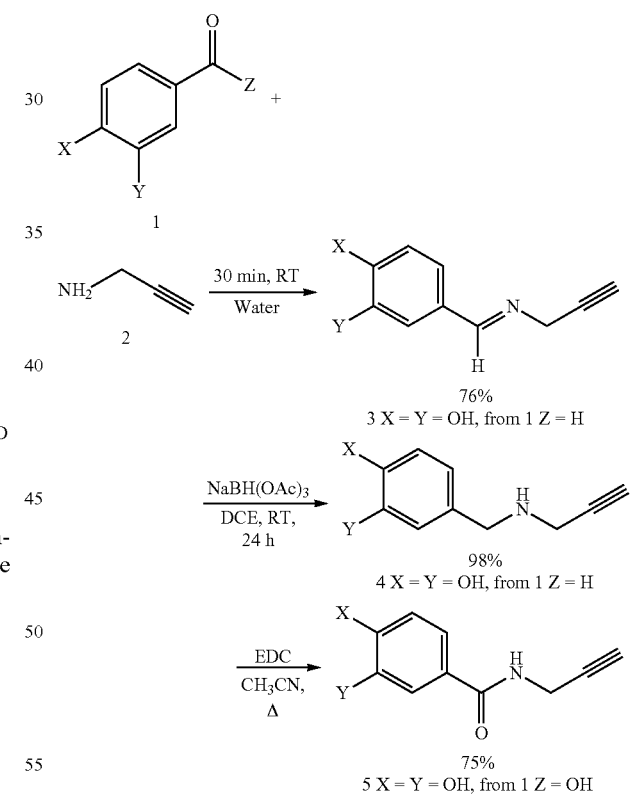

In some embodiments, 2-aminoethylmethacrylate may be used instead of propargylamine (as shown in Scheme 5) to make compounds of the present invention, which may be linked to a thiol modified alkyne by Michael addition. In some embodiments, Michael reaction acceptors may be used rather than or in addition to thiol alkyne click partners for polysaccharide (e.g., HA), gelatin and/or collagen modification. A Michael reaction acceptor may contain aromatic rings with hydrogen bonding functional groups. A commercially available bis catechol with an a, b unsaturated ester functional group is rosmarinic acid. The esters may not be as reactive as the enones in the Michael reaction chemistry. In some embodiments, benzoic acid may be reacted with 1-hydroxy-3-buten-2-one to provide the compound shown in Scheme 6 with A=O, B=H or with 1-amino-3-methyl-3-buten-2-one to provide the compound shown in Scheme 6 with A=NH, B=Me, thereby providing hydrogen bonding esters rather than the amines, imines, and amides. In some embodiments, such enones may be capable delivering hydrogen bonding catechols to HA without photolysis.

Scheme 6: Example compound of the present invention with enone linker.

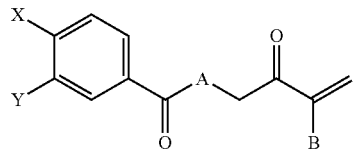

The foregoing and other aspects of the invention are explained further in the following examples.

EXAMPLES

Example 1

Representative Synthetic Procedures for Making Imines 1 equivalent of amine, 1.1 equivalents of aldehyde, a catalytic amount of p-toluene sulfonic acid, 0.1 mL of acetic acid and molecular sieves were placed in a flame dried RBF and dissolved in dry MeOH. The reaction was then refluxed with a dean stark trap for 48 to 72 hours.

The molecular sieves were filtered and the solvent removed by rotovap. The solids collected were then triturated in ethyl acetate for 15-20 minutes and filtered.

4-(2-((4-hydroxybenzylidene)amino)ethyl)benzene-1,2-diol (dopamine+4 hydroxybenzaldehyde)

The product was obtained as a white solid. $^1$H NMR (300 MHz, DMSO-d6) δ 11.47 (s, 1H), 8.84 (s, 2H), 8.62 (s, 1H), 8.09-8.00 (m, 2H), 7.08-6.99 (m, 2H), 6.68-6.62 (m, 2H), 6.48 (dd, J=8.0 Hz, 2.1 Hz, 1H), 3.88 (t, J=7.2 Hz, 2H), 2.91 (t, J=7.2 Hz, 2H). $^{13}$C NMR (75 MHz, DMSO-d$_6$) δ 168.3, 165.9, 145.3, 144.0, 135.1, 127.7, 119.5, 118.3, 116.9, 116.2, 115.6, 53.5, 33.8. High resolution mass spec (ESI M+1) Calculated for $C_{15}H_{15}O_3N$: 258.1130 found: 258.1121.

4-(2-((4-hydroxybenzylidene)amino)ethyl)phenol. (tyramine+4 hydroxybenzaldehyde)

The product was obtained as a pink solid. $^1$H NMR (300 MHz, DMSO-d$_6$) δ 13.28 (s, 1H), 11.55 (s, 1H), 8.63 (s, 1H), 8.09 (d, J=8.8 Hz, 2H), 7.04 (dd, J=9.6 Hz, 3.0 Hz, 4H), 6.71 (dd, J=9.0 Hz, 7.1 Hz, 2H), 3.91 (t, J=7.2 Hz, 2H), 3.00 (t, J=7.1 Hz, 2H). $^{13}$C NMR (75 MHz, DMSO-d$_6$) δ 168.4, 166.0, 156.1, 135.2, 129.8, 129.5, 128.1, 127.0, 125.4, 118.2, 116.8, 115.3, 53.3, 33.4, 32.1. High resolution mass spec (ESI M+1) Calculated for $C_{15}H_{15}O_2N$: 242.1181 found: 242.1173.

Example 2

Noncovalent Binding Polysaccharide Additives.

Imines can be synthesized from condensation of aldehydes and amines and anilines are known to condense with hydroxyl substituted benzaldehydes (Chen, W. et al. Synthesis and biological evaluation of hydroxyl-substituted Schiff-bases containing ferrocenyl moieties. Dalton Transactions 42, 15678-15686, doi:10.1039/C3DT51977E (2013); Cheng, L.-X. et al. Antioxidant and antiproliferative activities of hydroxyl-substituted Schiff bases. Bioorganic & Medicinal Chemistry Letters 20, 2417-2420, (2010)). Initially, 4 different imines from condensation reactions of 4-hydroxy and 3,4-dihydroxybenzaldehyes with tyramine and dopamine (Nador, et al., Coordination Polymer Particles with ligand-centred pH-responses and spin transition. Chemical Communications 50, 14570-14572, doi:10.1039/C4CC05299D (2014)) (1a-d) were prepared (1b,d unoptimized) and their qualitative testing is described below. A nice feature of aldehyde-amine condensation is that it can also be performed under reductive amination conditions to provide secondary amine products which will have additional hydrogen bonding and water solubility when needed. Additional small molecules that do not rely on the imine or amine functional group for linkage are described below. Chain length between the hydrogen bonding phenols and catechols as well as intermolecular interactions with a variety of linkers in addition to the hydroxybenzenes can be modified.

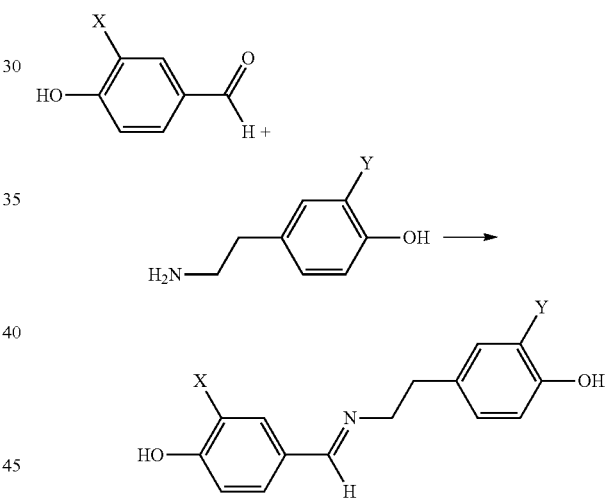

1a X = Y = H, 83%; 1b X = Y = OH, 23%; 1c X = H, Y = OH, 76%; 1d X = OH, Y = H, 12%

Covalent Bond Forming Polysaccharide Additives.

Initially, we chose to make some catechol containing alkynyl imines and amines since they could easily be added to thiolated HA via the thiol alkyne click reaction (Fairbanks, et al. Photopolymerizations: Novel Mechanism, Kinetics, and Step-Growth Formation of Highly Cross-Linked Networks. Macromolecules 42, 211-217, doi: 10.1021/ma801903w (2009); Skardal, A. et al. A hydrogel bioink toolkit for mimicking native tissue biochemical and mechanical properties in bioprinted tissue constructs. Acta Biomaterialia 25, 24-34, doi:http://dx.doi.org/10.1016/j.actbio.2015.07.030 (2015)). 3,4-Dihydroxybenzaldehyde was condensed with propargylamine to form both the imine and amine in excellent yields and the results of using these compounds in the thiol alkyne click reaction are described below.

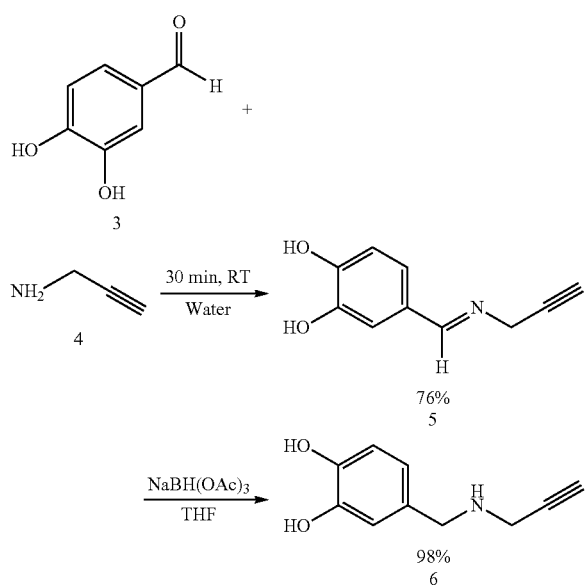

Preliminary Small Molecule Testing for Gelation and Adhesiveness.

Compounds 1a and 1c were dissolved in PBS at 100 mg/mL and observed qualitatively for any gelation or adhesive characteristics. 1c formed a viscous fluid, that is not quite a gel, which if pulled in 2 directions and then let go, would return to its original position, while, in comparison 1a did not seem truly crosslinked and when manipulated did not remain in one tight droplet. These compounds were then qualitatively tested for adhesiveness by tilting a Petri dish with droplets of the compounds. Both 1a and 1c, stayed in place, while PBS droplets instantly slid down the dish surface.

These early results appear to indicate adhesiveness. We believe by modulating the concentration of the compounds, as well as inclusion of other proposed materials (e.g. modified HA, or thiolated-HA compatible compounds) we will increase crosslinking between the catechol groups, and achieve materials with superior gelation and adhesion properties.

Figure 2:
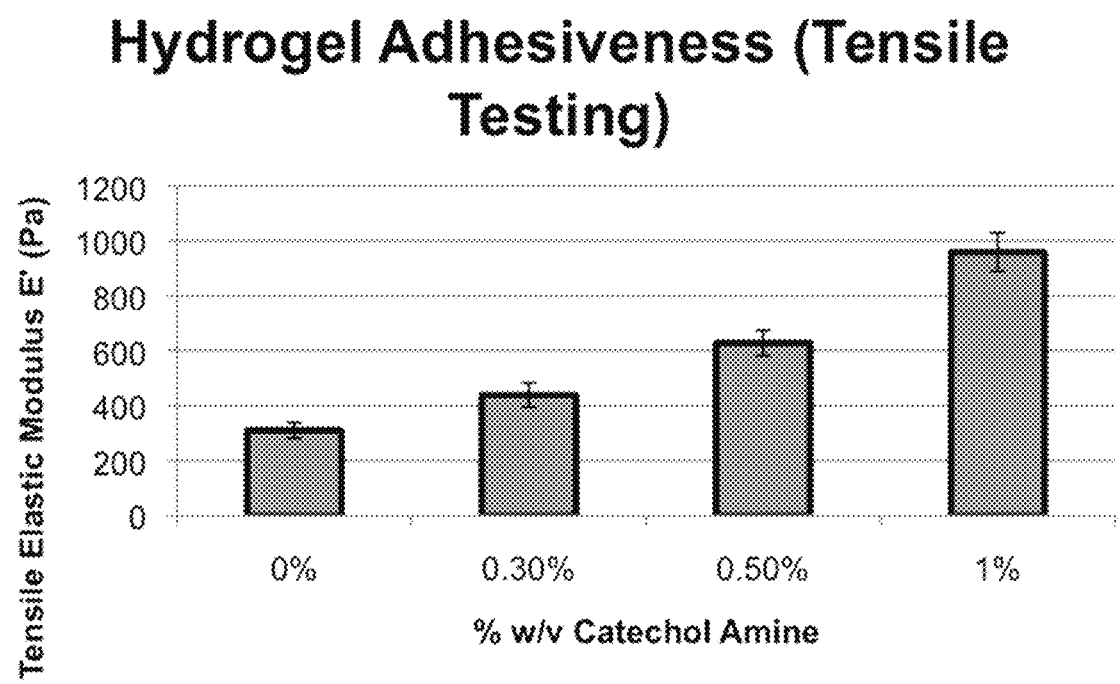
FIG. 2 shows a graph of the tensile testing data that demonstrates increases in adhesiveness as the amount of catechol amine is increased in the hydrogel.

Testing of preliminary molecules showed that addition of catechol amine compounds with linkable alkyne groups could be incorporated into the modular HA hydrogel system as shown in Scheme 1 via photopolymerizable coupling to thiol groups along the HA backbones and gelatin molecules. Importantly, hydrogen bonding between the catechol groups now covalently bound to the hydrogel network (via thiol-alkyne bonds) further increased the G' values of the hydrogel constructs (FIG. 1). These increases were not observed in control groups. This gives validation to the activity of the newly added catechol components of the system. In further testing of 6, we observed significantly more "stickiness" in the hydrogel constructs during mechanical shear testing runs. Following this observation we employed the rheometer using a customized protocol to apply a tensile stretch to hydrogels that had immobilized between the base and testing geometry of the rheometry. The geometry was brought into contact with the sample and lowered until 0.4 N normal force was reached by the load cell. At this point, the sample was allowed to equilibrate for 30 seconds, after which the rheometer applied constant displacement vertically at 5 um/s, raising the geometry 1000 um, during which time resistive force ("stickiness") was measured by the load cell every second. Preliminary test results showed a 3-fold increase in tensile resistance due to the increased adhesive nature of the catechol amine containing hydrogel (FIG. 2).

Example 3

Modified Hyaluronic Acids

Dopamine can be added to unmodified hyaluronic acid via amide coupling conditions but in our hands these reactions tend to yield HA with varying levels of dopamine incorporation (Shin, J. et al. Tissue Adhesive Catechol-Modified Hyaluronic Acid Hydrogel for Effective, Minimally Invasive Cell Therapy. Advanced Functional Materials 25, 3814-3824, doi:10.1002/adfm.201500006 (2015)). Nevertheless, having access to chemically modified HA in addition to commercially available material will allow us to have controls for comparison as well as new materials in which we can screen small molecule additives. Initially, we would also add 4-(2-aminoethyl) benzoic acid and 2-aminoethylmethacrylate (10) to hyaluronic acid (Borke, T., Winnik, F. M., Tenhu, H. & Hietala, S. Optimized triazine-mediated amidation for efficient and controlled functionalization of hyaluronic acid. Carbohydrate Polymers 116, 42-50, doi: 10.1016/j.carbpol.2014.04.012 (2015)) to prepare (11) so that mixtures of the small molecule additives can be tested and compared to unmodified HA and this modified HA. While not wishing to be bound to any particular theory, we hypothesize that integration of catechols with a bioactive HA backbone may result in a hydrogel material with 1) improved adherence to tissue, 2) increased elastic modulus and robustness due to the addition of catechol crosslinking, and 3) increased resistance to shear and tensile mechanical disruption, thereby serving as useful tissue adhesive and surgical glue, with the capability for therapeutic bioactivity that will be important upon implementation in future in vivo testing. In addition, while not wishing to be bound to any particular theory, we also hypothesize that use of small molecule additives to HA may result in materials via simpler synthesis and purification than existing HA chemical treatment followed by dialysis, with more reproducible properties. Catechols on the HA backbones also can be targeted for crosslinking using bi-functionalized compounds described above (ex. compounds 1a-1d).

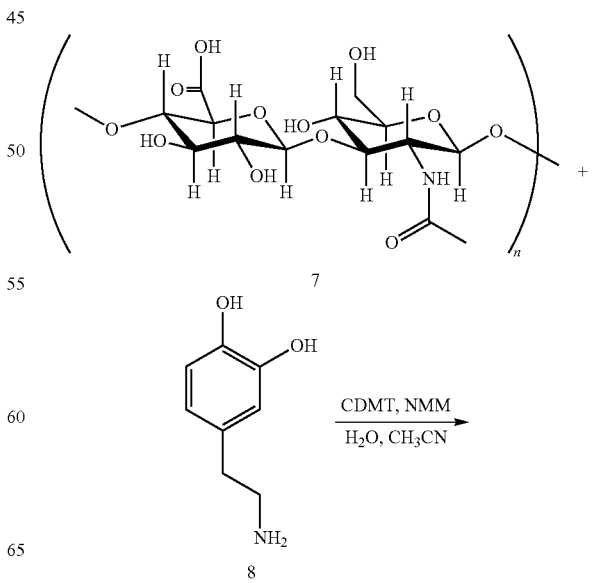

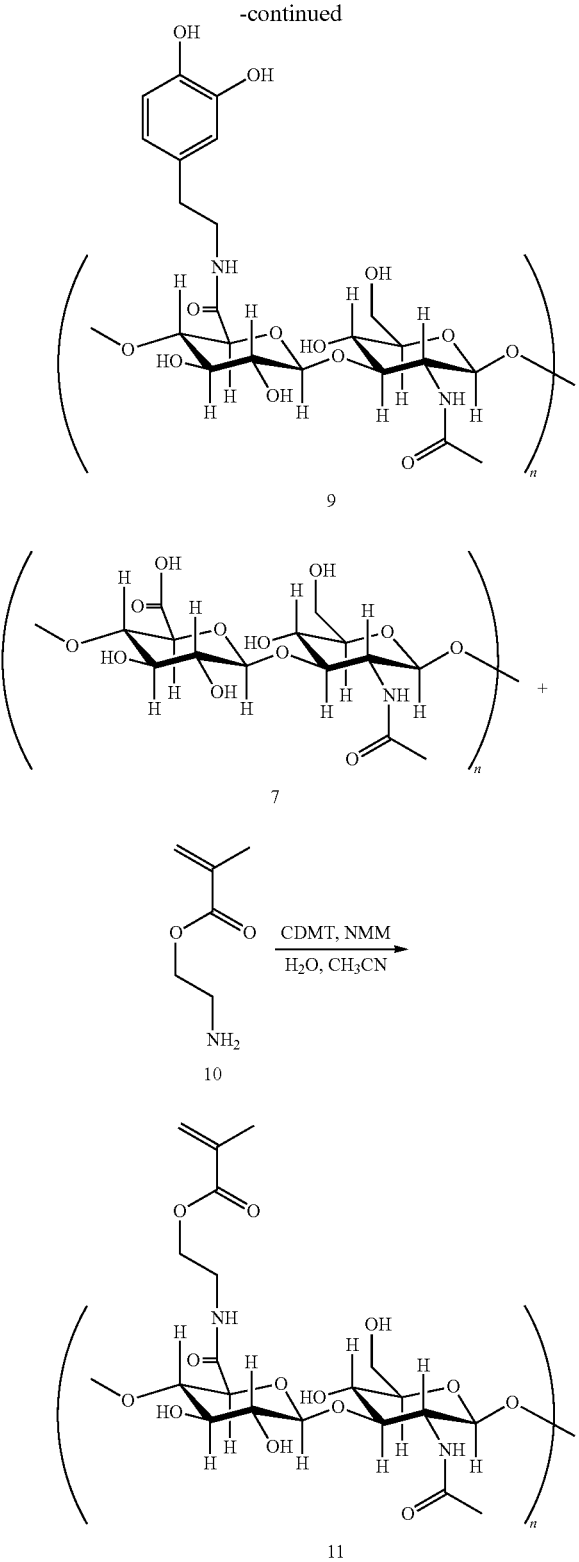

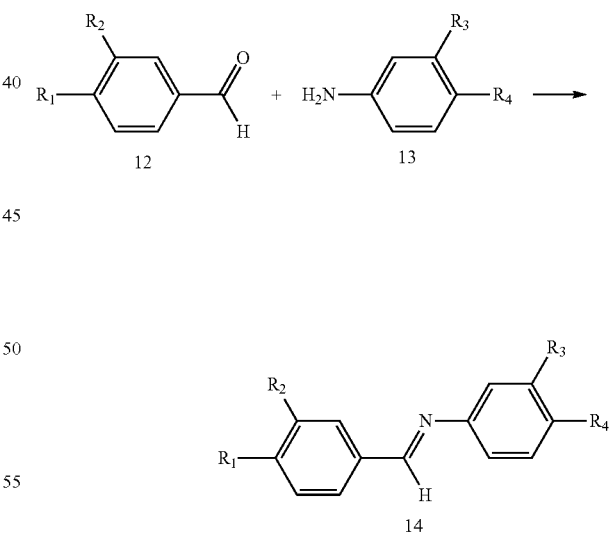

being synthesized to allow us to compare and contrast the modular addition of known amounts of small molecules to commercially available HA to covalent bond forming chemical modifications of HA noted above. As noted above, our hypothesis is that controlled additions of known amounts of small molecules will prove as effective or superior to the chemical modification of HA since it is much easier to prepare and purify the small molecules than it is the polysaccharides. We have initiated this synthetic work by preparing compounds (1a-d, 5, 6) as described above.

A variety of additional small molecules will be prepared. These are broken down into new noncovalent and covalent bond forming polysaccharide modifiers.

Noncovalent Binding Polysaccharide Additives

Condensation of anilines (13) rather than phenethylamines with aldehydes (12) ($R_1=R_2=H$ or OH) will allow us to determine the importance of the ethylamine group on additive properties. Use of 4-aminobenzoic acid (13) ($R_3=H$, $R_4=CO_2H$) as a coupling partner rather than a phenol or catechol will allow us to compare the properties of those groups to the hydrogen bonding and acid-base active carboxylic acid functional group (4-aminomethylbenzoic acid is also readily available if needed here). 3-Fluoro-4-hydroxybenzaldehyde and 4-amino-2-fluorophenol are also readily available and they would allow for studies to ascertain how the strong C—F bond dipole affects the properties of these molecules.

Beyond these initial studies there are many additional possibilities. Reductive amination as described above for 6 would give us the amines to compare to imines (14) and we already have preliminary data that indicates the water solubility (and potentially additional hydrogen bonding ability) of the amines is an advantage. Amides (17) can be prepared (Gao, et al., FeBr3-Catalyzed Tandem Reaction of N-Prop-

Example 4

Small Molecule Development as Modular Components in Hydrogel Systems

In conjunction with the development of modified polysaccharide materials, a number of new small molecules are argylamides with Disulfides or Diselenides for the Synthesis of Oxazole Derivatives. Synlett 27, 1110-1115, doi:10.1055/s-0035-1561202 (2016)), and it is proposed that a comparison be made between them and amides (e.g., 3-Fluoro-4-hydroxybenzoic acid is also readily available here in addition to compounds (15) where R1, R2 or both R1 and R2 are OH). Anilines and phenethylamines are attractive as nucleophiles in these condensations due to their ready availability but it will also be possible for us to compare the benzene system to the cyclohexane system in the nucleophiles via use of amines like trans-4-aminocyclohexanol and trans 4-aminomethylcyclohexane carboxylic acid.

forming reactions described next. Diamines like phenylene diamine or xylene diamine could also be used as coupling partners and yield a benzene linker to compare to alkane linkers. All new small molecule organic compounds prepared will be characterized by $^1$H and $^{13}$C NMR and elemental analysis or HRMS. New HA's prepared will be characterized by $^1$H NMR to assess the extent of functionalization and dynamic light scattering (DLS) techniques to assess polymer size. Yields for chemical reactions are based on at least three repetitions.

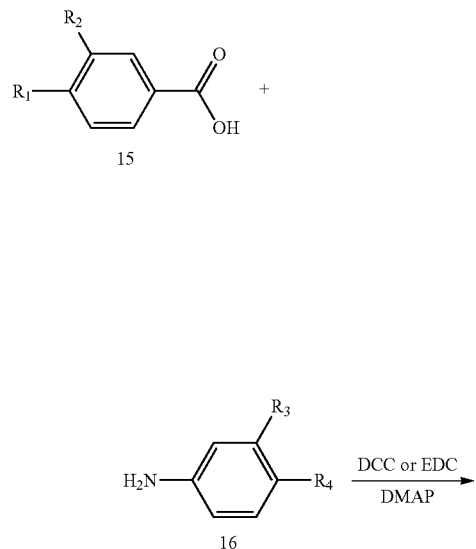

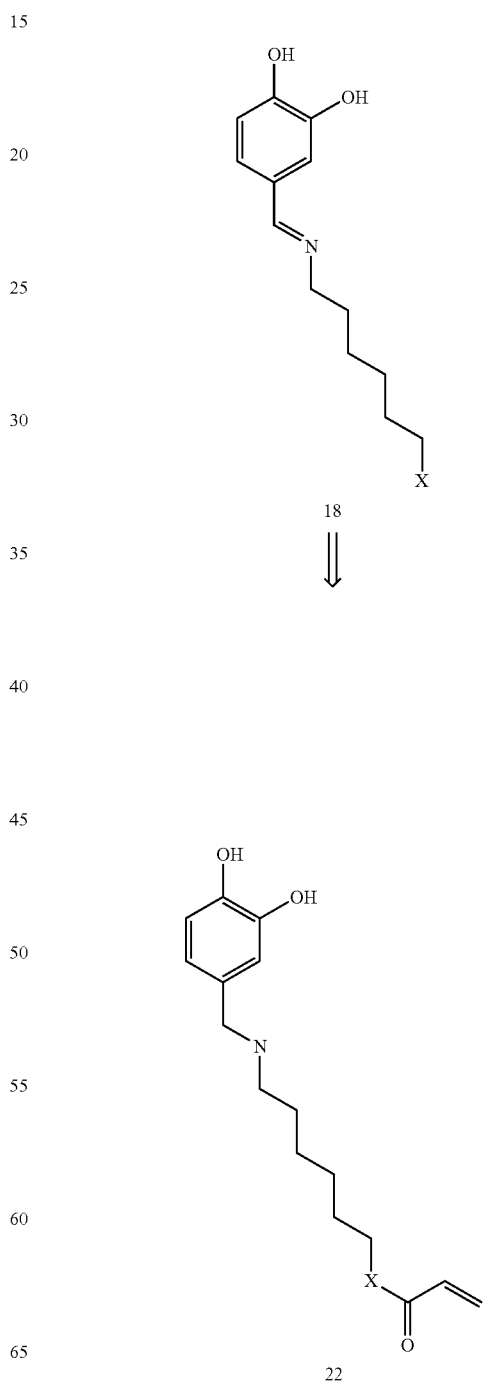

Three component rather than two component coupling reactions would next be studied. Amino alcohols (or diamines) could be coupled with aldehydes or acids (18, 19 X=OH or NH$_2$, aminohexanol or hexanediamine is shown here but others could be used). Compounds 18-21 would allow us to test an alcohol versus amine and ester versus amide with HA. When X=OH we would also have the option of converting compounds 18 and 19 into acrylates (22) and alkynes (23) which could be used in the covalent bond -continued

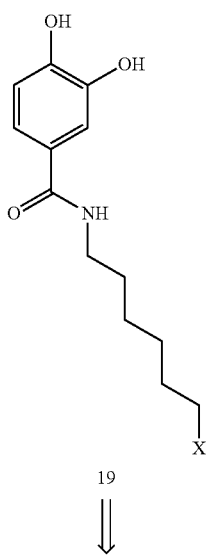

19

⇩

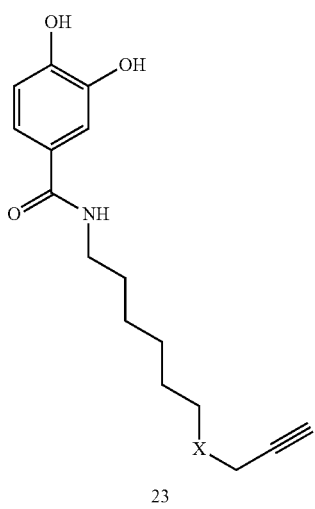

23

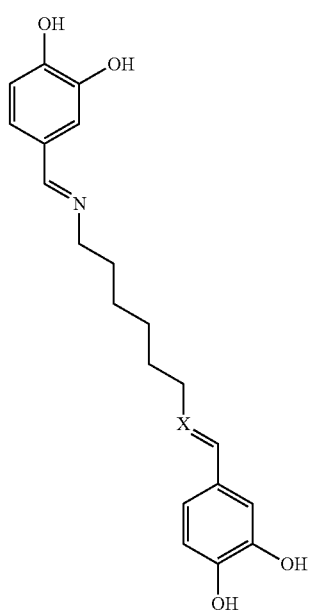

-continued

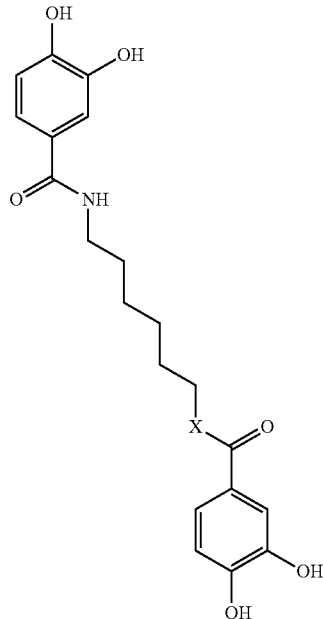

21

Covalent Bonding Polysaccharide Additives

Additives that can form covalent bonds with HA by mechanisms other than oxidative catechol dimerization (Šmejkalová, D., Conte, P. & Piccolo, A. Structural Characterization of Isomeric Dimers from the Oxidative Oligomerization of Catechol with a Biomimetic Catalyst. Biomacromolecules 8, 737-743, doi:10.1021/bm060598o (2007)) fall into 2 major categories: alkynes such as the first 2 (5 and 6) we described above in addition to compounds like 23 and acrylates such as 22 which we also show above. Since alkynyl catechols (26) are readily available via Sonogashira couplings of terminal alkynes (25) onto halogenated catechols (24) (Olivi, N., Spruyt, P., Peyrat, J.-F., Alami, M. & Brion, J.-D. Tandem amine propargylation-Sonogashira reactions: new three-component coupling leading to functionalized substituted propargylic amines. Tetrahedron Letters 45, 2607-2610, doi:http://dx.doi.org/10.1016/j.tetlet.2004.01.141 (2004)) we plan to make and test two other categories of alkyne compounds as covalent bond forming additives: catechols+alkynes+primary alcohols and amines. Those primary alcohol and amine functional groups can then be used to add other catechols via imine or amide forming reactions in the case of the amine and via ester linkages in the case of the alcohol to yield compounds like 28. They will also be used to add acrylates as we show here to produce additives (27) that could form covalent bonds by thiol alkyne or Michael addition reactions. Testing of compounds that could add by thiol alkyne addition and present 2 catechol groups will also be evaluated via 30.

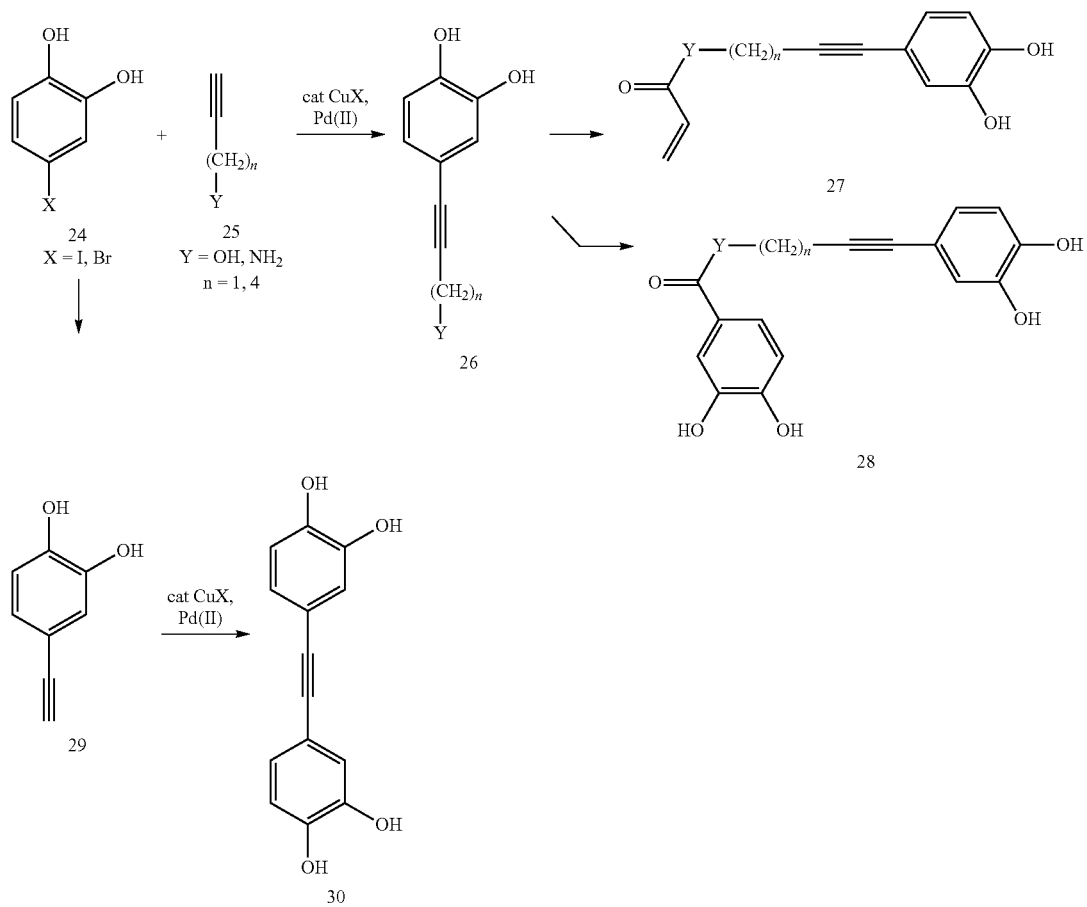

Hydrogel Formulations and Small Molecule Integration

In general, 2 primary categories of HA hydrogel formulations will be tested. 1) Native HA modified with catechols described above in various concentrations; and 2) a thiolated HA system, in which compounds containing alkyne or acrylate functional groups will be incorporated as supplements in several concentrations to several concentrations of the HA hydrogel system.

For Approach 1, the modified HA compounds will be dissolved in PBS. Additional formulations will be tested in which complexes formed by HA-catechols interact with monofunctional and bi-functional catechols.

For Approach 2, thiolated HA (conjugated heparin groups optional) and thiolated gelatin will be dissolved in water containing 0.05% w/v 2-hydroxy-4'-(2-hydroxyethoxy)-2-methylpropiophenone photoinitiator (Sigma) to make 1, 2, or 5% w/v solutions. A PEGDA (polyethylene glycol diacrylate) crosslinker or multi-arm PEG-acrylate crosslinker, will dissolved in water containing the photoinitiator to make a 2, 4, or 10% w/v solution. The HA, gelatin, and crosslinker components will then mixed in a 2:2:1 ratio by volume, vortexed and irradiated with UV light (365 nm, 18 w/cm$^2$) to initiate a nearly instantaneous crosslinking reaction. Catechol acrylate, catechol methacrylate, or catechol alkyne compounds will be supplemented prior to crosslinking in a range of test concentrations. The acrylate/methacryate/alkyne functional groups on these compounds serve to support seamless covalent integration into this thiol- and acrylate-based polymer network system (Scheme 1).

Hyaluronic Acid Mechanical Testing:

Mechanical bulk properties. Hydrogels will be formed in custom molded 12 mm dishes and assessed by rheology to determine bulk material shear elastic modulus. We will empirically measure G' of hydrogel formulations with an 8 mm diameter parallel plate geometry by using shear stress sweep tests ranging from 0.6 to 20 Pa at an oscillation frequency of 1 Hz applied by WFIRM's Discovery HR-2 rheometer (TA Instruments) as has been described previously (Skardal, A., Zhang, J., McCoard, L., Oottamasathien, S. & Prestwich, G. D. Dynamically crosslinked gold nanoparticle—hyaluronan hydrogels. Adv Mater 22, 4736-4740, doi:10.1002/adma.201001436 (2010); Skardal, A., Zhang, J. & Prestwich, G. D. Bioprinting vessel-like constructs using hyaluronan hydrogels crosslinked with tetrahedral polyethylene glycol tetracrylates. Biomaterials 31, 6173-6181, doi:S0142-9612(10)00561-2 [pii]10.1016/j.biomaterials.2010.04.045 (2010); Skardal, A. et al. Photocrosslinkable hyaluronan-gelatin hydrogels for two-step bioprinting. Tissue Eng Part A 16, 2675-2685, doi:10.1089/ten.TEA.2009.0798 (2010); and Vanderhooft, J. L., Alcoutlabi, M., Magda, J. J. & Prestwich, G. D. Rheological properties of cross-linked hyaluronan-gelatin hydrogels for tissue engineering. Macromol Biosci 9, 20-28, doi:10.1002/mabi.200800141 (2009)). Testing of preliminary molecules (6) showed that addition of catechol amine compounds with linkable alkyne groups could be incorporated into the modular HA hydrogel system described above via photopolymerizable coupling to thiol groups along the HA backbones and gelatin molecules. Importantly, hydrogen bonding between the catechol groups now covalently bound to the hydrogel network (via thiol-alkyne bonds) further increased the G' values of the hydrogel constructs (FIG. 1).

Mechanical shear testing. The performance of catechol-HA hydrogels as tissue adhesives will be analyzed by shear tests performed on an Instron mechanical testing machine. Dehydrated porcine dermis procured from cadavers will be reconstituted in PBS to serve as tissue. The tissues will be immobilized onto the machine fixtures and joined using the catechol-HA tissue adhesive. Shear forces will be applied using a tensile test protocol causing the tissue pieces to be sheared apart from one another. Samples will be strained until failure, after which stress-strain curves and elastic modulus measurements will be assessed based on adhesive-tissue cross-sectional area. This methodology has been previously established in wound healing studies at WFIRM. Fibrin glue will be employed as a control.

Mechanical tensile testing. Additionally, the performance of catechol-HA hydrogels will be analyzed by tensile tests performed on the same Instron machine. For more sensitive testing, we will employ a customized setup and protocol that is run on the Discovery HR-2 rheometer using its high sensitivity load cell that is capable of capturing lower force values. For tensile testing the experimental setup will be similar, prepared and oriented so that the adhesive is no longer being sheared, but is instead directly below the first tissue piece and above the second tissue piece. Again, dehydrated porcine dermis procured from cadavers will be reconstituted with PBS to serve as tissue. The tissues will be glued or immobilized onto the machine fixtures and joined using the catechol-HA tissue adhesive. Tensile forces will be applied using a tensile test protocol causing the tissue pieces to be pulled away from one another. Samples will be strained until failure, after which force measurements will be assessed based on adhesive-tissue cross-sectional area. Again, fibrin glue will be employed as a control.

Extrusion testing. The compounds will be tested for extrusion capabilities. Extrusion is an often-overlooked characteristic of new biomaterial systems. For wound healing and surgical adhesive applications, a key product feature is the ability of a material to be easily extruded from a single syringe or double canister mixing syringe by the surgeon or physician into or onto the target site. We intend these materials to have real world application, and as such, we will assess extrusion in the lab through a range of needle sizes. We see the compounds described in this proposal as potentially having superior extrusion capabilities through either shear thinning or thixatropic properties, making them potential candidates for bioprinting testing.

Biocompatibility testing. The compounds in hydrogel systems will be tested to verify appropriate biocompatibility characteristics. Specifically, hydrogels will be employed as 1) substrates for "2D-on-top" cultures and 2) 3D encapsulation cultures using a toolbox of cell lines commonly used for biocompatibility screening. We will employ HepG2 liver hepatoma cells, Int-407 intestine epithelial cells, HUVEC endothelial cells, and NIH 3T3 fibroblasts, (Skardal, A., Zhang, J., McCoard, L., Oottamasathien, S. & Prestwich, G. D. Dynamically crosslinked gold nanoparticle—hyaluronan hydrogels. Adv Mater 22, 4736-4740, doi:10.1002/adma.201001436 (2010); Skardal, A., Zhang, J. & Prestwich, G. D. Bioprinting vessel-like constructs using hyaluronan hydrogels crosslinked with tetrahedral polyethylene glycol tetracrylates. Biomaterials 31, 6173-6181, doi: S0142-9612(10)00561-2 [pii]10.1016/j.biomaterials.2010.04.045 (2010); Skardal, A. et al. Photocrosslinkable hyaluronan-gelatin hydrogels for two-step bioprinting. Tissue Eng Part A 16, 2675-2685, doi: 10.1089/ten.TEA.2009.0798 (2010); and Zhang, J., Skardal, A. & Prestwich, G. D. Engineered extracellular matrices with cleavable crosslinkers for cell expansion and easy cell recovery. Biomaterials 29, 4521-4531, doi:S0142-9612(08) 00565-6 [pii]10.1016/j.biomaterials.2008.08.008 (2008)) and assess prolonged proliferation over the course of 7-14 days by MTS mitochondrial metabolic assays. Additionally, LIVE/DEAD staining and fluorescent imaging will be employed to visualize the ratios of viable to dead cells. In future studies, more sensitive cell types such as primary cells or iPS-derived differentiated cells may be used based on the final application of the developed materials.

Example 5

A hyaluronic acid and gelatin hydrogel system was explored to be subject to development towards an adhesive hydrogel product. Catecholamine and amide compounds were specially synthesized with alkyne functional groups to the exploit the well-established thiol-yne 'click' chemistry. The catecholamine and amide compounds when coupled to the gelatin/hyaluronic acid backbone provide extraneous moieties for hydrogen bonding that effect the hydrogel's self-adhesion and substrate adhesion properties. Furthermore, the cost efficient and easily synthesized small molecules afford tuneability to the hydrogel's rheological and viscid (adhesive) properties while maintaining great atom economy, no additional curing agents or additives, and an overall low molecular loading molecular capacity. In addition, the photo-initiated, radical-mediated crosslinking method to form the hydrogel is catalyzed by a non-yellowing, non-metallic compound (Irgacure 2959®) which maintains the gel's transparency and thus remains ideal for in situ or in vivo microscopic imaging. Our data suggest that this novel approach to hydrogel tuneability through small molecule addition is worth further exploration in the development of a biocompatible surgical adhesives and regenerative medicine.

General Experimental Design

For this study, we employed a two-step photo-initiated, radical-mediated polymerization technique to create a HA-based hydrogel matrix. Catecholamine compounds were synthesized that could provide additional hydrogen bonding interactions and adhesiveness to the matrix. For the integration of catecholamine compounds into our hydrogel matrix we used thiol-yne "click" chemistry, similar to the thiol-ene "click" chemistry already in place in the HyStem® hydrogel system (ESI-BIO, Alameida, Calif.). Material testing was performed, e.g., rheological testing (shear-stress sweep) and adhesive testing (tensile strength).

Synthesis of 2-(3,4-dihydroxyphenyl)-N-(2-proynl) acetyl (catecholaminoalkyne, C1.1)

For catecholaminolkyne synthesis, first 3,4-dihydroxybenzaldehyde (500.0 mg, 3.62 mmol, 1.0 eq) was suspended in 15 mL of dry DCE. Subsequently, propargylamine (347 µL, 5.43 mmol, 1.5 eq) was added dropwise and stirred for 30 minutes at r.t. under inert conditions. Sodium triacetoxyborohydride (2.148 g, 10 mmol, 2.8 eq) was added and allowed to react for 24 hours. No purification methods followed and resulted in an isolated yield of 98%. The synthesis of the compound was confirmed with 1H-NMR and 13C-NMR (Section S1). Scheme 7 provides the reaction schematic.

Scheme 7: Reaction for the synthesis of catecholaminoalkyne (C1.1).

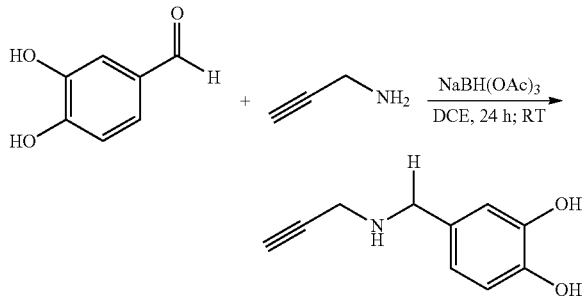

Synthesis of
2-(3,4-dihydroxyphenyl-N-(2-propynyl)acetamide
(catecholamidoalkyne, C1.2)

For catecholamidoalkyne synthesis, 3,4-dihydroxybenzoic acid (1.00 g, 6.49 mmol, 1.0 eq) was first dissolved in 30 mL of acetonitrile and was followed by the dropwise addition of propargylamine (831.3 µL, 12.9 mmol, 2 eq). 1-Ethyl-3-(3-dimethylaminopropyl)carbodiimide (1.21 g, 7.79 mmol, 1.2 eq) was slowly added and the resulting reaction was refluxed at 70° C. for 3 hours. Once completed, the compound was purified by column chromatography (silica gel, solvent gradient of 50%, 80% and 100% EtOAc in pentane), with an isolated yield of 75%. The synthesis of the compound was confirmed with 1H-NMR and 13C-NMR (Section S1). Scheme 8 provides the reaction schematic.

Scheme 8: Reaction for the synthesis of catecholamidoalkyne (C1.2).

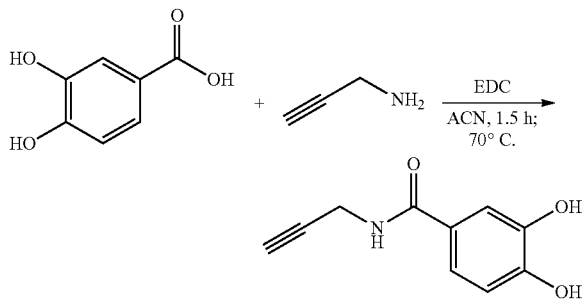

Synthesis and Modification HyStem® Hydrogel System

To a 2 mL centrifuge tube, 200 µL of Heprasil® solution (1% w/v solution, thiolated HA component of HyStem kit), 200 µL of Gelin-S® solution (1% w/v, thiolated gelatin component of HyStem kit), 50 µL of Extralink® solution (2% w/v, polyethylene glycol diacrylate component of HyStem kit), and 50 µL of a modular catecholamine (C1.1) or amide (C1.1) solutions (0.25%-1.5% w/v, see Rheology section for specifics) were added and mixed by softly pipetting the solution up and down carefully to avoid creating bubbles. For control experiments the modular catecholamide or amine solutions were replaced with an equivalent volume of sterile deionized water. For rheology or cell culture studies, the reaction mixture was placed into wells of an appropriate size and exposed to UV radiation (~222 nm) for 1-5 seconds. FIG. 8 shows the reaction schematic and chemical diagram.

Rheological Studies

A Discovery HR-2 Rheometer (TA Instruments, New Castle, Del.) with an 8 mm geometry was used to collect the rheological data. After reaction set-up, 200 µL of the reaction mixture was transferred into a 12 mm diameter×5 mm depth PDMS well. The PDMS well containing the reaction mixture was then exposed to UV radiation for 5 seconds at a distance of 1 cm. Photo-initiated polymerization and formation of a hydrogel occurred instantaneously. To ensure standard conditions across all experiments the geometry was lowered into the gels until a calibration normal force of 0.4N was achieved. Following, an oscillatory shear-stress sweep test (0.6-10.0 Pa, 1.0 Hz, 25° C.) was applied to hydrogels containing varying concentrations (0%, 1.0%, and 1.5% w/v) of modular amine compounds, C1.1 and C1.2. This experiment was repeated in triplicate for each condition. Average shear elastic modulus, G', values were determined for each condition.

Tensile Strength Studies

A Discovery HR-2 Rheometer (TA Instruments) with an 8 mm geometry was used to collect the tensile strength, T', data. The test was designed to quantify the axial force (Pa) exerted by the hydrogel on the geometry as measured by the rheometer as the geometry is slowly raised over 2000 µm at 25° C. The absolute value of the axial force (Pa) was then taken to be the adhesive force or tensile strength T' (Pa) assigned to the hydrogel. To ensure standard conditions across all experiments the geometry was lowered into the gels until a calibration force of 0.4N was observed. Following, a rheometer tensile strength test was applied to the hydrogels at each of the respective conditions containing varying concentrations (0% w/v, 0.25% w/v, 0.50% w/v, and 1.0% w/v) of modular amine compounds, C1.0-C1.2. This experiment was repeated in triplicate for each condition.

Cell Culture 2.0 mL cryogenic vials (stored at −196° C.) containing 1.0 mL of 20% DMSO in Dulbecco's Minimum Essential Medium+10% fetal bovine serum+1% penicillin-streptomycin solution (DMEM, Sigma, St. Louis, Mo.; FBS, Hyclone, Logan, Utah; PS, Gibco) at a cell density of 1×10^6 cells-mL-1 of HepG2 (HB-8065, ATCC, Manassas, Va.) and Caco2 (HTB-37, ATCC, Manassas, Va.) epithelial cell lines, respectively, were thawed in a 37° C. water bath, respectively. Once thawed the cell mixtures were seeded on separate 15 cm culture plate and 15 mL of DMEM-10-1 was added to each plate. The seeded plates were placed in an incubator (37° C., 6.0% CO2) for the cells to adhere and proliferate until reaching a 90% confluency on the plate.

Cell Characterization

At the proper confluency, the plates were washed with 10 mL of DPBS followed by an addition of 5 mL of trypsin and a 5 min incubation time at 37° C. Upon the conclusion of the incubation time light microscopy was used to determine that the cells had become detached. 5 mL of DMEM-10-1 was added to the plate and the trypsin/DMEM mixture was transferred into a 15 mL conical tube. A 1:4:5 ratio of cell mixture/DMEM-10-1/trypan blue was created in a 2.0 mL cryogenic vial. The mixture contained ~1.2×105 cells-mL-1. The cells were pelleted down by centrifugation at 1500 rpm for 5 minutes and the trypsin/DMEM mixture was aspirated. The cells were resuspended in 10 mL of DMEM-10-1. For the MTS assay, 3.0×104 cells per well were seeded (In total 2.43×106 cells are needed for 81 wells). In each well (n=3 per time point) of a 96 well plate 16 µL of Heprasil® (1 mg-mL-1, 1% w/v), 16 µL of Gelatin-S® (10 mg-mL-1, 1% w/v), 4 μL of Extralink® (5 mg 0.250 μL-1, 2% w/v), and 4 μL of modular catecholamine (1 mg-mL-1, 3.6 mM, 1% w/v), C1.1 and C1.2, respectively were mixed by gently pipetting the solution up and down. The wells were then exposed to UV radiation (~222 nm) for 3 seconds at distance of 1 cm to initiate crosslinking and form the hydrogel matrix. Approximately 30,000 cells were seeded per well; 200 μL of DMEM+10% FBS+1% pen-strep media at a density of $1.2\times10^5$ cells-mL-1 were aliquoted into each well, Caco-2 and HepG2 cell lines, respectively. A total of 27 wells per time point (3 per condition-positive control, catecholamine (C1.1), and catecholamide (C1.2) for each cell line, Caco-2 and HepG2. For the 3D cell cultural technique and amount of cells used in the live/dead assay refer to the Live/Dead Assay section.

MTS Assay

The MTS assay is widely-used as a nonradioactive quantification of cellular proliferation, viability, and cytotoxicity.28 The MTS assay based on the reduction of MTS tetrazolium compound by viable cells to generate a colored formazan product that is soluble in cell culture media. This conversion is thought to be carried out by NAD(P)H-dependent dehydrogenase enzymes in metabolically active cells. MTS assays were performed using a CellTiter 96® AQueous One Solution Cell Proliferation Assay (G3582, Promega) at days 1, 4, 7. First, the media was aspirated from each well and subsequently washed with 200 μL DPBS and removed. The wells were then incubated with 200 μL of pre-equilibrated DMEM-10-1 containing 15% MTS reagent for 45 minutes at 37° C. A color transition from a lighter to darker red was observed. At the conclusion of the 45-minute incubation period a Molecular Device SpectraMax M5 plate reader was used to determine the optical density of each well monitored at 490 nm. At each time point conditions were set up in triplicate (n=3). All results reported here are the averaged normalized optical density (OD) for n=3 runs at each condition, Ctrl, C1.1 and C1.2. Reported uncertainties were calculated using the standard deviations between the normalized OD values for n=3 runs of each condition.

Live/Dead Assay $3.0\times10^6$ HepG2 and Caco-2 cells were harvested from the tissue culture dishes, respectively. Following, they were centrifuged into cell pellets and the supernatant was discarded. For each cell line, HepG2 and Caco2, three conditions were prepared, i.e., a positive control (HyStem®) and two experimental conditions (HyStem®+C1.1 and HyStem®+C1.2). To prepare each condition, a $3.0\times10^6$ cell pellet was suspended in 500 μL 1% w/v Heprasil®, 500 μL 1% w/v Gelatin-S®, 125 μL of 2% w/v Extralink®, and 125 μL of 1% w/v C1.1/C1.2 (experimental conditions) or 125 μL of sterile, deionized water (positive control). The final cell density for each condition was $3.0\times10^6$ cells-mL-1. One 50 μL sample of each hydrogel condition at each condition was aliquoted into a 96-well for each time point (1, 4, and 7 days). A LIVE/DEAD™ Cell Imaging Kit (488/570) (Invitrogen™) was used. At each time point media was aspirated from the wells and were subsequently incubated for 45-60 min with 200 μL of DPBS containing 4 mM of calcein AM and 2 mM of ethidium homodimer. Live cells fluoresce green due to the uptake and hydrolysis of calcein AM, and the nuclei of dead cells are labelled by the red-fluorescent ethidium homodimer.

Red vs Green Pixel Analysis

A MATLAB (MathWorks®) script (supplemental information, S.3) was used to quantify red and green fluorescent signals generated by biochemical interactions between the ethidium homodimer and calcein AM, and cells, respectively.

Statistical Analysis

In general, Microsoft Excel was used to generate all graphs and statics. All results are reported here as the mean+/−standard deviation. All results were subjected to a t-Test: Paired Two Sample for Means assuming unequal variance. $p<0.05$ was considered statistically significant.

Figure 3:
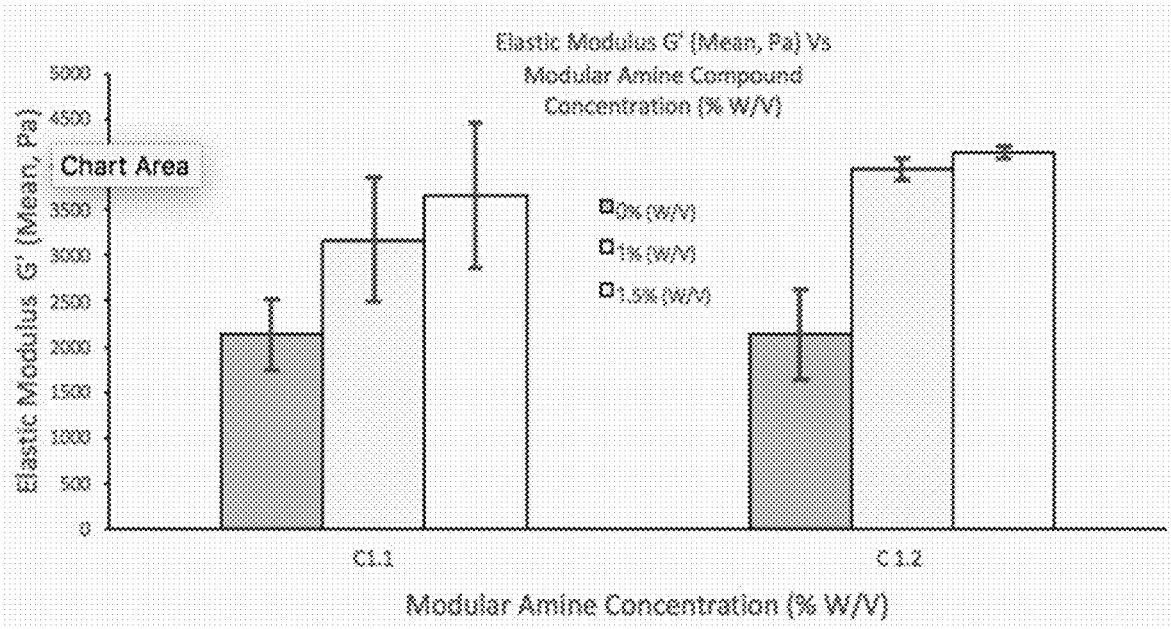
FIG. 3 shows a graph of Elastic Modulus G' (Pa) Vs Modular Amine (C1.1/C1.2) Solution Concentration (% w/v). Reported here is the averaged G' value for (n=3) runs at (0%, 1.0% and 1.5% w/v) for each compound. Reported uncertainties were calculated using the standard deviations between the averaged G' values within (n=3) runs of each concentration. p<0.05.
Figure 4:
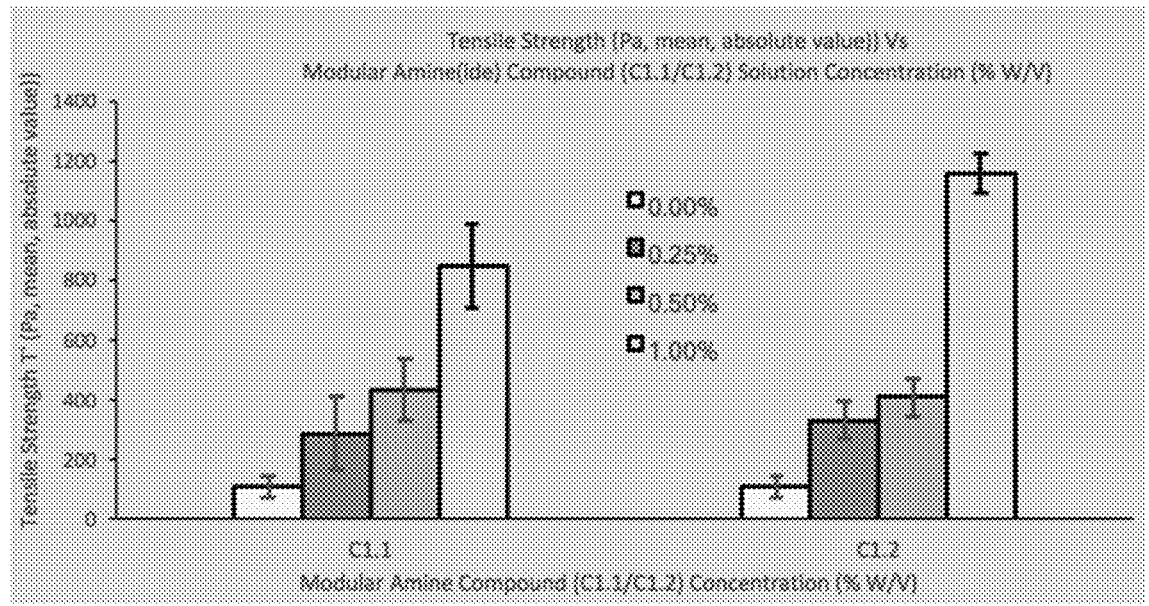
FIG. 4 shows a graph of Tensile Strength T' (Pa) Vs Modular Amine (C.1/C1.2) Solution Concentration (% w/v). Reported here is the average Tensile Strength T' value (Pa) for n=3 runs at 0%, 0.25%, 0.50%, 1.0% w/v for each compound, C1.1 and C1.2. Reported uncertainties were calculated using the standard deviations between the averaged T' values (Pa) for n=3 runs at each concentration. **p<0.05.

Shear-stress sweep tests (0.6-10.0 Pa, 1.0 Hz, 25° C.) were applied to hydrogels containing varying solution concentrations (0%, 1.0%, and 1.5% WAV) of modular amine compounds, C1.1/C1.2. Reported here are the average shear elastic modulus G' values for n=3 runs for each condition (FIGS. 3 and 4). The reported uncertainties were calculated from standard deviations between n=3 averaged G' values of each condition. In FIG. 3 we report the following G' values: $(2.136\times10^3+/-3.988\times10^2)$ Pa for the HyStem® control, $(3.166\times10^3+/-6.772\times10^2)$ Pa for the HyStem®+1% w/v catecholamine, and $(3.648\times10^3+/8.047\times10^2)$ Pa for the HyStem®+1.5% w/v catecholamine. This indicates an approximate $(1.029\times10^3+/-3.280\times10^1)$ Pa increase in G' when to the comparing the HyStem® control to the 1.0% w/v C1.1 condition. Furthermore, the comparison of the HyStem® control to the 1.5% w/v C1.1 condition indicates a $(1.512\times10^3+/-3.469\times10^1)$ Pa increase in the G' value observed. Thus it was observed that when increasing the % w/v of the catecholamine (C1.1) solution used from 0% w/v, 1% w/v, 1.5% w/v, a proportional increase in G' was observed, i.e., 1 equivalent of C1.1=1000 Pa increase in G' and 1.5 equivalent=1500 Pa increase in the G' of the hydrogel matrix.

In a parallel study, shear elastic modulus G' data was collected for gels while increasing the % w/v of the catecholamide (C1.2) from 0% w/v, 1.0% w/v, and 1.5% w/v, we collected the following G' values: $(2.136\times10^3+/-4.885\times10^2)$ Pa for Hystem® control, $(3.953\times10^3+/-1.160\times10^2)$ Pa for the 1.0% w/v HyStem®+1% w/v catecholamine, and $(4.125\times10^3+/7.406\times10^1)$ Pa for the HyStem®+1.5% w/v catecholamine. This indicates an approximate $(1.817\times10^3+/-2.457\times10^1)$ Pa increase in G' when comparing the HyStem® control to the 1.0% w/v C1.2 condition. Furthermore, the comparison of the HyStem® control to the 1.5% w/v C1.2 condition indicates a $(1.989\times10^3+/-1.378\times10^1)$ Pa increase in the G' value observed.

Although, in both cases containing a 1.0% and 1.5% w/v solution of C1.1 and C1.2 for a similar increase in the G' was observed; the gels containing a 1.0% w/v C1.2 solution showed a 788 Pa higher increase in the G' over gels containing a 1.0% w/v C1.1 solution. In addition, gels containing a 1.5% w/v C1.1 solution showed a 477 pa increase over gels containing a 1.0% w/v C1.1 condition. While not wishing to be bound to any particular theory, our assumption here is that increased intermolecular interactions are occurring with the C1.2. In addition to the ortho-dihydroxyl groups offered by the catechol moiety, the amide moiety offers an extra hydrogen donor species, the carbonyl oxygen ($C=O$), for intermolecular interactions between the adjacent catecholamides. The catecholamides located on different HA chains or gelatin increase the ability for the hydrogel matrix to both interact with itself and other substrates through hydrogen bonding. Whereas the amine (C1.1) has a secondary carbon in the same position as the carbonyl functional group on the amide (C1.2), we postulate that the lack of this hydrogen bonding position yields a lower increase in G' observed in hydrogel when comparing the two compounds. Again, to ensure standard conditions across all experiments, the geometry was lowered into the gels until a calibration force of 0.4N was detected. Following, a tensile strength test (25 μm/s, 2000 m, 25° C.) was applied to hydrogels containing varying concentrations (0%, 0.25%, 0.75%, and 1.0% w/v) of modular amine solutions, C1.1/C1.2. The reported values are the average T' (Pa) values for n=3 runs at every condition and uncertainties were calculated from standard deviations between n=3 averaged T' (Pa) for each condition. In FIG. 4, we report the following T' (Pa) values for hydrogels containing C1.1: $(1.10 \times 10^2 +/- 2.91 \times 10^1)$ Pa for Hystem® control, $(2.90 \times 10^2 +/- 1.23 \times 10^2)$ Pa for Hystem®+0.25% w/v catecholamine, $(4.25 \times 10^2 +/- 1.01 \times 10^2)$ Pa for Hystem® +0.50% w/v catecholamine, and $(8.48 \times 10^2 +/- 1.42 \times 10^2)$ Pa for Hystem®+1.0% w/v catecholamine. This indicates that each time the concentration of catecholamine was doubled, i.e., moving from 0.25% to 0.50% to 1.0% w/v an approximate 100% increase in T' (Pa) was observed. For example, a $(4.13 \times 10^2 +/- 1.56 \times 10^1)$ Pa increase in T' is observed when comparing the Hystem®+0.50% w/v catecholamine to the Hystem®+1.0% w/v catecholamine. In addition, we collected the following T' values (Pa) for hydrogels containing C1.2: $(1.09 \times 10^2 + 3.64 \times 10^1)$ Pa for Hystem® control, $(3.33 \times 10^2 +/- 6.16 \times 10^1)$ Pa for Hystem®+0.25% w/v catecholamide, $(4.12 \times 10^2 +/- 6.39 \times 10^1)$ Pa for Hystem®+0.50% w/v catecholamide, and $(1.16 \times 10^3 +/- 6.34 \times 10^1)$ Pa for Hystem®+1.0% w/v catecholamide. Furthermore, the catecholamide (C1.2) aided in superior adhesive qualities over the catecholamine (C1.1) conditions; a 200% increase was observed in the T' (Pa) values when doubling the concentrations of the C1.2 present, i.e., a $(7.48 \times 10^2 +/- 1.13 \times 101)$ Pa increase in the T' value when comparing the Hystem®+0.50% w/v catecholamide to the Hystem®+1.0% w/v catecholamide. Conclusively, we can say the increase in allotted tensile strength T' (Pa) of the hydrogels when cross comparing compounds, C1.1 and C1.2, is due to the amide moiety having higher hydrogen bonding capacities.

The robust adhesive nature of our hydrogel is exhibited by our specifically designed the tensile strength test. Importantly, at a concentration of 1.0% w/v for the catecholamine (ide) solution used we observed an approximately 4 and 6-fold increase in the tensile strength T' (Pa) exhibited by the hydrogels containing C1.1 and C1.2, respectively.

In both cases, the higher degree to which the G' and T' increased when comparing the catecholamine (C1.1) vs catecholamide (C1.2) conditions. It could be argued that this increase in the G' and T' could simply be attributed to increasing the density of the hydrogel, given the increase in molecular mass present over the same volume; however, the molecular weights for the thiolated HA, thiolated gelatin, and diacyrlate polyethylene glycol are disproportionately higher than that of our catecholamine (C1.1) or catecholamide (C1.2) compounds. Although, the increases in the shear elastic modulus G' for our HA-based hydrogel is modest in comparison to commercially available CA polymers, G'>45 kPa7, this hydrogel has a final 1% w/v concentration of all material. Therefore, the observation that such small modifications, i.e., increasing the % w/v of catecholamine (C1.1) or catecholamide (C1.2) with respect to volume of solvent can affect the shear elastic modulus G' (Pa) and tensile strength T'(Pa) in such a way is rather astonishing. It appears this highly tunable platform has many yet unlocked properties, for which we will explore.

For the hydrogels consisting of HyStem® and HyStem®+ 1% w/v C1.1, in each case following their rheological characterization, at the conclusion of the shear-stress test the geometry was raised out of the gel at a rate of 100 μm/s over a range of 2000 μm. The use of low loading capacities of high molecular weight HA, Gelatin, and PEGDA, maintains large pore sizes (20-100 μm) within the hydrogel matrix which is conducive of proper cell migration and proliferation.

In addition, minimal material usage is always optimal, especially in the realm of surgical adhesives, as it is both cost-effective and will undoubtedly reduce an immune response elicited by an organism. One concern addressed by the formulation we report here is that our hyaluronic acid (HA), gelatin, polyethylene glycol diacrylate (PEGDA), and catecholamine/amide-based polymeric hydrogel does not produce cytotoxic byproducts such as the formaldehyde given off by CA polymers. Indeed, degradation of the hydrogel occurs and is wanted, however the byproducts of this process themselves are non-toxic. To modulate the rheological and viscid properties of our hydrogel we have developed a simple method for incorporating small molecules into the HA/Gelatin/PEGDA hydrogel matrix.

Cell Viability Studies

In the course of developing new biocompatible surgical adhesives in vitro cell-viability experiments were employed to confirm the cytocompatible natures of the materials. Live/Dead assays were used to qualitatively visualize and quantitatively report 3D cell proliferation within the hydrogels. Epithelial cell lines, HepG2 and Caco2, were used due to being well-characterized, susceptible to in vitro modeling, and their resilient nature. The use of multiple cell lines which were subjected to the same conditions strengthen the biocompatibility study and provide evidence for widespread application among potential tissue types. Images were captured using a Leica DMi8 inverted microscope.

Live/Dead Studies

Figure 5:
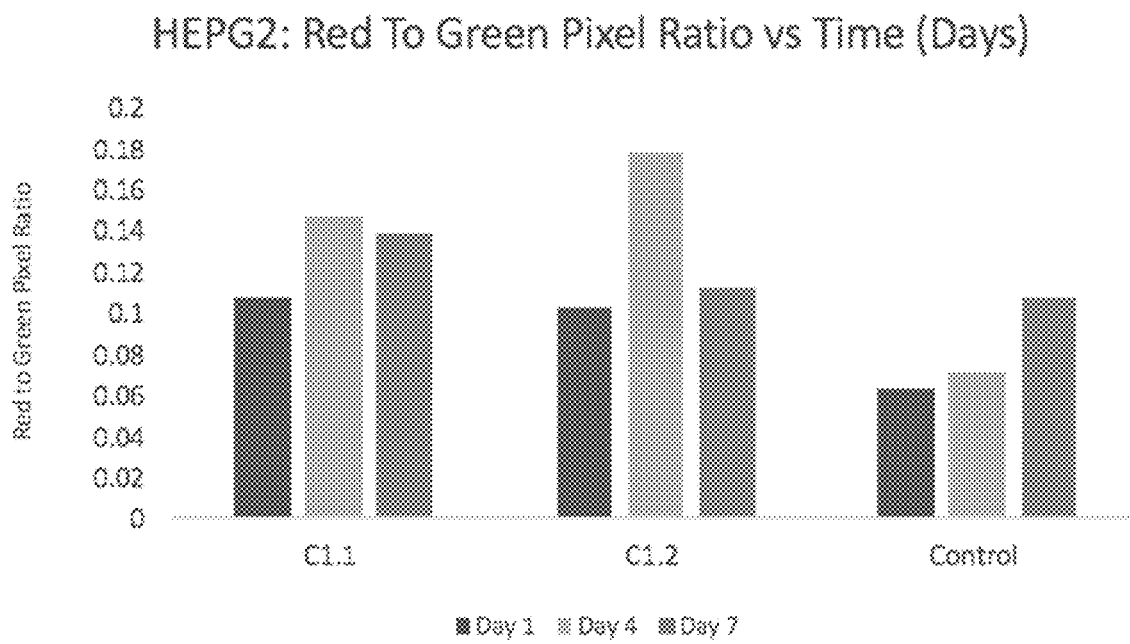
FIG. 5 is a graph of the 7-Day 3D Live/Dead Image Pixel Analysis for HepG2. *C1.1=1:1 volume ratio of 1% w/v catecholamine aqueous solution to 2% w/v PEGDA aqueous solution. C1.2=1:1 volume ratio of 1% w/v catecholamide aqueous solution to 2% w/v PEGDA aqueous solution. Control=1:1 volume ratio of sterile, deionized water to 2% w/v PEGDA aqueous solution. The concentrations of HA and Gelatin solutions were kept constant at 1% w/v for all conditions.
Figure 6:
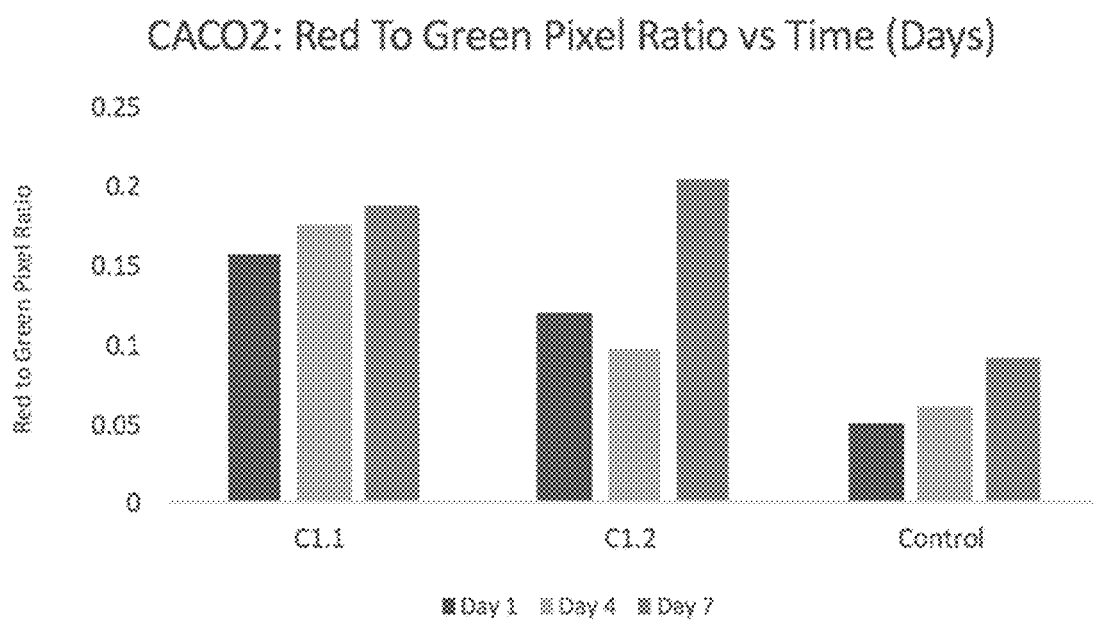
FIG. 6 is a graph of the 7-Day 3D Live/Dead Image Pixel Analysis for Caco-2. *C1.1=1:1 volume ratio of 1% w/v catecholamine aqueous solution to 2% w/v PEGDA aqueous solution. C1.2=1:1 volume ratio of 1% w/v catecholamide aqueous solution to 2% w/v PEGDA aqueous solution. Control=1:1 volume ratio of sterile, deionized water to 2% w/v PEGDA aqueous solution. The concentrations of HA and Gelatin solutions were kept constant at 1% w/v for all conditions.

The Hystem® hydrogel system is well-established as a hydrogel with biocompatible properties. It has been highlighted in literature for its cell-viability in such applications as tissue engineering, drug encapsulation, and biomaterials numerous times over the past 10-15 years. The Hystem® hydrogel used as positive control maintained great cell-viability and proliferation over days 1, 4, and 7. In addition, both experimental groups, hydrogels with C1.1 and C1.2, were shown to have only a slightly depressed biocompatibility when compared to the positive control, Hystem® system, yet overall, cells remained viable. Quantification of the red (dead) and green (viable) pixels was performed using an image processing script written on MATLAB (S.3). In this case, the live cell staining corresponds with the cytoplasm of the cell while the dead stain only highlights the nuclei of the cell therefore we use the ratio of red to green pixels as a quantification to show the relative cell-viability rather than report individual Live/Dead cell quantification over time. FIGS. 5 and 6, depict this ratio for the HepG2 and Caco-2 cell lines, respectively. We show that the ratio of red to green pixels remained relatively constant over that same time period for each condition. This suggests that our hydrogels are not only providing a 3D extracellular environment which is biocompatible, but that over time the cell populations migrate, proliferate, and the system is cyto-friendly.

MTS Assays

Figure 7:
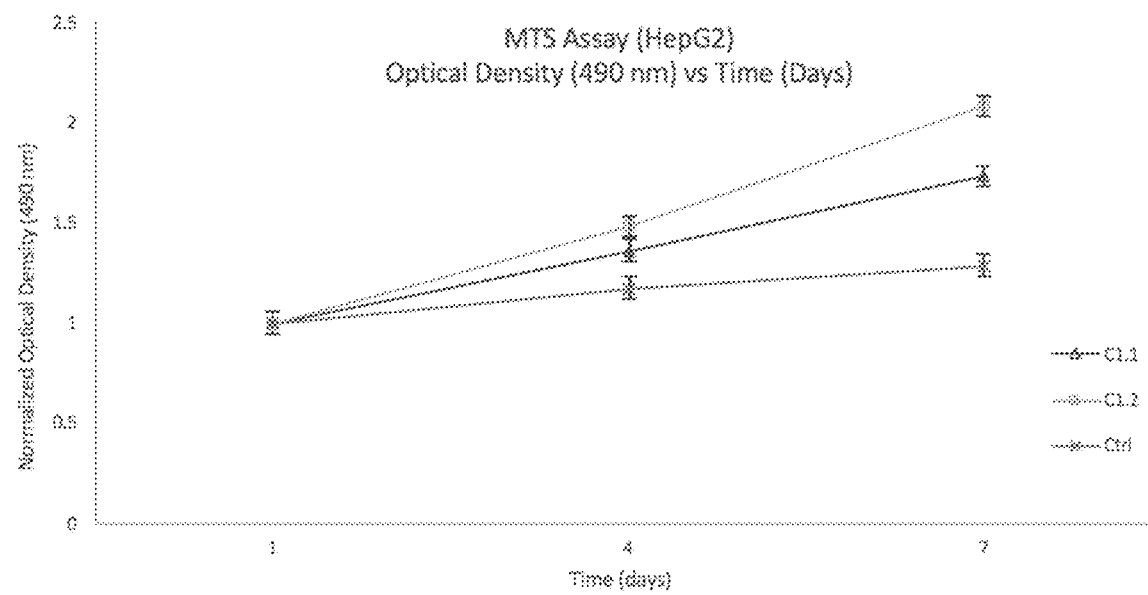
FIG. 7 shows a graph (top) for 2D 7-day MTS Assay for quantification of the HepG2 proliferation at conditions: C1.1, C1.2, and Control*, and a graph (bottom) for 2D 7-day MTS Assay for quantification of the Caco-2 proliferation at the same conditions. *C1.1=1:1 volume ratio of 1% w/v aqueous solution of catecholamine to 2% w/v aqueous solution of PEGDA. C1.2=1:1 volume ratio of 1% w/v aqueous solution of catecholamide to 2% w/v aqueous solution of PEGDA. Control=1:1 volume ratio of sterile, deionized water to 2% w/v aqueous solution of PEGDA. Reported here is the averaged normalized optical density (OD) for n=3 runs at each condition, Ctrl, C1.1 and C1.2. Reported uncertainties were calculated using the standard deviations between the normalized OD values for n=3 runs at each condition. **p<0.05.
Figure 7:
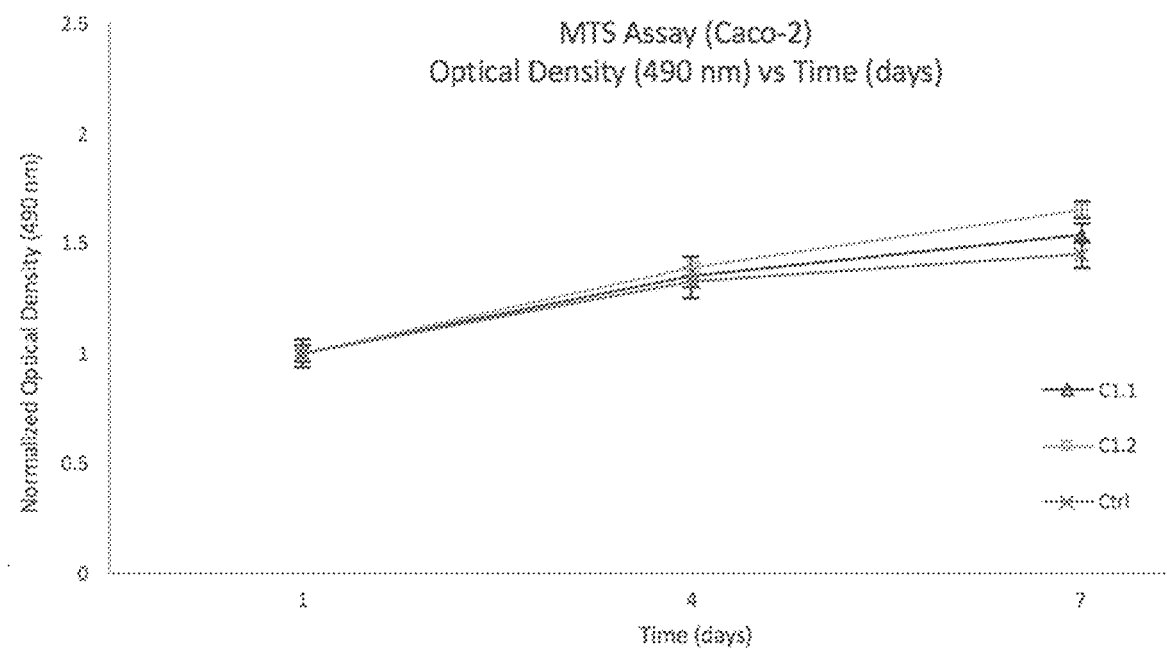

In addition to Live/Dead assays, MTS assays were used to quantify the proliferation of cells. In this case, the ability for cells to proliferate in 2D when seeded on the hydrogels was assessed. FIG. 7 demonstrates proliferation kinetics for HepG2 and Caco2 cells—used in the above Live/Dead studies—indicating that the hydrogel environment supports great cell proliferation over the 7-day incubation shown through the use of MTS assays.

Interestingly, the optical density was shown to be higher for conditions C1.1 and C1.2, when compared to the control. This could potentially be accounted for by the increasing rigidity of the hydrogels when treated with catecholamine and catecholamides. It has been shown that epithelial cell migration is optimization of pore size within hydrogels. In many cases epithelial cells, as well as stem cells and cancer cells, prefer more a rigid environment for adherence proliferation. Therefore, with the increase of intermolecular interactions through hydrogen bonding of adjacent catecholamines or amides our hydrogels increase in rigidity and the cell proliferation is increased.

It appears that increasing the number of available hydrogen bond acceptor moieties, e.g., replacing the secondary amine functional group (R2N—H) for the amide functional group (R(CO)N—H) within our small molecule additives increased the tensile strength and adhesive strength of the hydrogel matrix. This methodology for increasing both the shear elastic modulus G' (Pa) and tensile strength T'(Pa) of HA-based hydrogels may be exploited for the fabrication of biomedical devices and multifunctional biomaterials such as bioinks.

The foregoing is illustrative of the present invention, and is not to be construed as limiting thereof. The invention is defined by the following claims, with equivalents of the claims to be included therein. All publications, patent applications, patents, patent publications, and other references cited herein are incorporated by reference in their entireties for the teachings relevant to the sentence and/or paragraph in which the reference is presented.

That which is claimed is:

1. A modified polysaccharide comprising at least one polysaccharide unit including a moiety having a structure represented by Formula IV or Formula V:

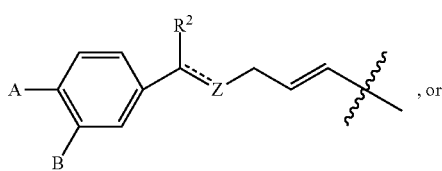

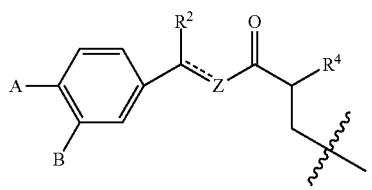

wherein
A and B are each independently selected from the group consisting of hydrogen, —OH, chlorine, fluorine, —CO$_2$H, —CO$_2$CH$_3$, —NH$_2$, and —NHCOCH$_3$;
Z is —NR$_3$(CH$_2$)$_p$—, —O(CH$_2$)$_p$—, —NR$_3$(CH$_2$)$_p$O—, —NR$_3$(CH$_2$)$_p$NR$_3$—;
R$^2$ is hydrogen or =O;
R$^3$ is hydrogen or is absent;
R$^4$ is hydrogen or C$_1$-C$_4$ alkyl; and
p is an integer from 0 to 11.

2. The modified polysaccharide of claim 1, wherein the modified polysaccharide is hyaluronic acid.

3. The modified polysaccharide of claim 1, wherein the moiety is bound to the at least one polysaccharide unit via a thiol linkage to provide a structure represented by Formula IV' or Formula V':

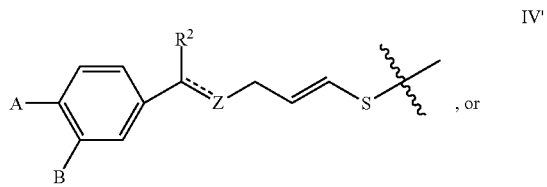

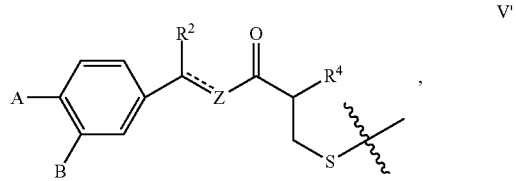

wherein
A and B are each independently selected from the group consisting of hydrogen, —OH, chlorine, fluorine, —CO$_2$H, —CO$_2$CH$_3$, —NH$_2$, and —NHCOCH$_3$;
Z is —NR$_3$(CH$_2$)$_p$—, —O(CH$_2$)$_p$—, —NR$_3$(CH$_2$)$_p$O—, —NR$_3$(CH$_2$)$_p$NR$_3$—;
R$^2$ is hydrogen or =O;
R$^3$ is hydrogen or is absent;
R$^4$ is hydrogen or C$_1$-C$_4$ alkyl; and
p is an integer from 0 to 11.

4. The modified polysaccharide of claim 1, wherein the moiety has a structure selected from the group consisting of:

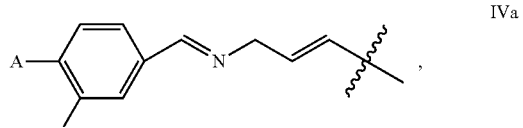

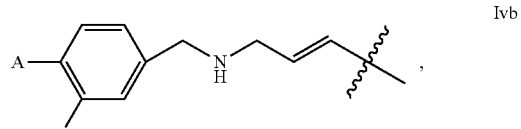

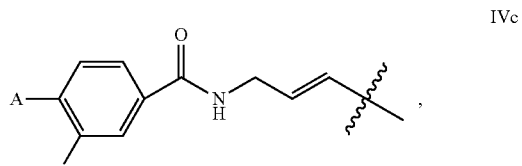

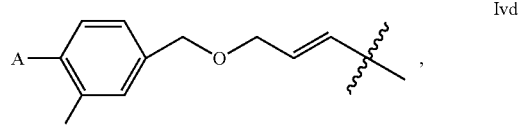

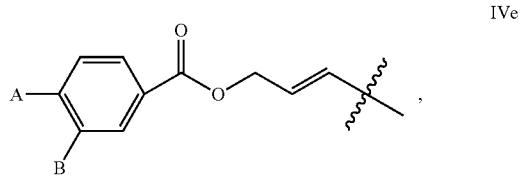

wherein A and B are each independently selected from the group consisting of hydrogen, —OH, chlorine, fluorine, —CO$_2$H, —CO$_2$CH$_3$, —NH$_2$, and —NHCOCH$_3$.

5. The modified polysaccharide of claim 1, wherein the moiety has a structure selected from the group consisting of:

wherein A and B are each independently selected from the group consisting of hydrogen, —OH, chlorine, fluorine, —CO$_2$H, —CO$_2$CH$_3$, —NH$_2$, and —NHCOCH$_3$; and R$^4$ is hydrogen or C$_1$-C$_4$ alkyl.

6. The modified polysaccharide of claim 5, wherein R$^4$ is methyl.

7. The modified polysaccharide of claim 5, wherein R$^4$ is hydrogen.

8. A modified gelatin comprising at least one moiety bound to the gelatin backbone via a thiol linkage to provide a structure represented by Formula IV' or Formula V':

wherein

A and B are each independently selected from the group consisting of hydrogen, —OH, chlorine, fluorine, —CO$_2$H, —CO$_2$CH$_3$, —NH$_2$, and —NHCOCH$_3$;

Z is —NR$_3$(CH$_2$)$_p$—, —O(CH$_2$)$_p$—, —NR$_3$(CH$_2$)$_p$O—, —NR$_3$(CH$_2$)$_p$NR$_3$—;

R$^2$ is hydrogen or =O;

R$^3$ is hydrogen or is absent;

R$^4$ is hydrogen or C$_1$-C$_4$ alkyl; and p is an integer from 0 to 11.

* * * * *

UNITED STATES PATENT AND TRADEMARK OFFICE
CERTIFICATE OF CORRECTION

| | | |
|---|---|---|
| PATENT NO. | : 11,286,231 B2 | Page 1 of 1 |
| APPLICATION NO. | : 16/344452 | |
| DATED | : March 29, 2022 | |
| INVENTOR(S) | : Welker et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 384 days.

Signed and Sealed this
Twenty-ninth Day of November, 2022

Katherine Kelly Vidal
*Director of the United States Patent and Trademark Office*